(12) United States Patent
Newby et al.

(10) Patent No.: US 9,339,741 B2
(45) Date of Patent: May 17, 2016

(54) DENSITY PHASE SEPARATION DEVICE

(71) Applicant: Becton, Dickinson and Company, Franklin Lakes, NJ (US)

(72) Inventors: C. Mark Newby, Tuxedo, NY (US); Christopher A. Battles, Seymour, CT (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 85 days.

(21) Appl. No.: 14/268,384

(22) Filed: May 2, 2014

(65) Prior Publication Data

US 2014/0238930 A1    Aug. 28, 2014

Related U.S. Application Data

(63) Continuation of application No. 12/506,841, filed on Jul. 21, 2009.

(60) Provisional application No. 61/082,361, filed on Jul. 21, 2008.

(51) Int. Cl.
| | |
|---|---|
| *B01L 3/14* | (2006.01) |
| *B01D 21/00* | (2006.01) |
| *B01L 3/00* | (2006.01) |
| *G01N 33/49* | (2006.01) |

(52) U.S. Cl.
CPC .......... *B01D 21/0084* (2013.01); *B01L 3/50215* (2013.01); *G01N 33/491* (2013.01); *B01L 2200/0631* (2013.01); *B01L 2300/042* (2013.01); *B01L 2400/049* (2013.01); *B01L 2400/0409* (2013.01)

(58) Field of Classification Search
CPC ..... B01L 3/50; B01L 3/5021; B01L 3/50215; B01L 3/502; B01L 3/508; B01L 3/5082; B01L 3/567; B01L 2300/049; B01L 2300/042; B01L 2200/0631; B01L 2400/0409; B01L 2400/06; B01D 21/0084; G01N 33/491

See application file for complete search history.

(56) References Cited

U.S. PATENT DOCUMENTS

| | | |
|---|---|---|
| 2,577,780 A | 12/1951 | Lockhart |
| 3,300,051 A | 1/1967 | Mitchell |
| 3,326,215 A | 6/1967 | Sarnoff et al. |

(Continued)

FOREIGN PATENT DOCUMENTS

| | | |
|---|---|---|
| AT | 414209 B | 10/2006 |
| DE | 2749130 A1 | 5/1979 |

(Continued)

*Primary Examiner* — David C Mellon
(74) *Attorney, Agent, or Firm* — The Webb Law Firm

(57) ABSTRACT

A mechanical separator for separating a fluid sample into first and second phases is disclosed. The mechanical separator includes a float having a first portion and a second portion, a ballast circumferentially disposed about a section of the float, and a deformable bellows defining an open passageway extending between a first end and a second end. The ballast is longitudinally moveable with respect to the float and engaged with the deformable bellows between the first end and the second end. At least a portion of the float is transitionable from a restraint position to a sealed position through the first end of the bellows. The first portion of the float can be positioned within the interior of the deformable bellows in the restraint position, and the first portion of the float can be positioned at an exterior location longitudinally displaced from the deformable bellows in the sealed position.

16 Claims, 16 Drawing Sheets

(56) References Cited

U.S. PATENT DOCUMENTS

| | | |
|---|---|---|
| 3,508,653 A | 4/1970 | Coleman |
| 3,543,338 A | 12/1970 | Cooper |
| 3,647,070 A | 3/1972 | Adler |
| 3,654,925 A | 4/1972 | Holderith |
| 3,661,265 A | 5/1972 | Greenspan |
| 3,741,400 A | 6/1973 | Dick |
| 3,771,965 A | 11/1973 | Grams |
| 3,773,450 A | 11/1973 | Svanfors |
| 3,779,383 A | 12/1973 | Ayres |
| 3,780,935 A | 12/1973 | Lukacs et al. |
| 3,786,985 A | 1/1974 | Blaivas |
| 3,800,947 A | 4/1974 | Smith |
| 3,809,733 A | 5/1974 | Sandiford et al. |
| 3,814,248 A | 6/1974 | Lawhead |
| 3,814,258 A | 6/1974 | Ayres |
| 3,832,110 A | 8/1974 | Hehl |
| 3,849,072 A | 11/1974 | Ayres |
| 3,850,174 A | 11/1974 | Ayres |
| 3,852,194 A | 12/1974 | Zine, Jr. |
| 3,862,042 A | 1/1975 | Ayres |
| 3,879,295 A | 4/1975 | Glover et al. |
| 3,882,021 A | 5/1975 | Ayres |
| 3,886,928 A | 6/1975 | Sarstedt |
| 3,887,464 A | 6/1975 | Ayres |
| 3,887,465 A | 6/1975 | Ayres |
| 3,887,466 A | 6/1975 | Ayres |
| 3,890,237 A | 6/1975 | Welch |
| 3,890,954 A | 6/1975 | Greenspan |
| 3,891,553 A | 6/1975 | Ayres |
| 3,894,950 A | 7/1975 | Ayres et al. |
| 3,894,951 A | 7/1975 | Ayres |
| 3,894,952 A | 7/1975 | Ayres |
| 3,897,337 A | 7/1975 | Ayres |
| 3,897,340 A | 7/1975 | Ayres |
| 3,897,343 A | 7/1975 | Ayres |
| 3,901,219 A | 8/1975 | Kay |
| 3,909,419 A | 9/1975 | Ayres |
| 3,919,085 A | 11/1975 | Ayres |
| 3,920,549 A | 11/1975 | Gigliello et al. |
| 3,920,557 A | 11/1975 | Ayres |
| 3,929,646 A | 12/1975 | Adler |
| 3,931,018 A | 1/1976 | North, Jr. |
| 3,932,277 A | 1/1976 | McDermott et al. |
| 3,935,113 A | 1/1976 | Ayres |
| 3,941,699 A | 3/1976 | Ayres |
| 3,945,928 A | 3/1976 | Ayres |
| 3,947,176 A | 3/1976 | Rainville |
| 3,951,801 A | 4/1976 | Ayres |
| 3,957,654 A | 5/1976 | Ayres |
| 3,960,727 A | 6/1976 | Hochstrasser |
| 3,969,250 A | 7/1976 | Farr |
| 3,970,565 A | 7/1976 | Ahlstrand et al. |
| 3,972,812 A | 8/1976 | Gresl, Jr. |
| 3,981,804 A | 9/1976 | Gigliello |
| 4,001,122 A | 1/1977 | Griffin |
| 4,004,868 A | 1/1977 | Ohdate |
| 4,021,340 A | 5/1977 | Zine, Jr. |
| 4,021,352 A | 5/1977 | Sarstedt |
| 4,027,660 A | 6/1977 | Wardlaw et al. |
| 4,055,501 A | 10/1977 | Cornell |
| 4,057,499 A | 11/1977 | Buono |
| 4,077,396 A | 3/1978 | Wardlaw et al. |
| 4,082,085 A | 4/1978 | Wardlaw et al. |
| 4,083,788 A | 4/1978 | Ferrara |
| 4,088,582 A | 5/1978 | Murty et al. |
| 4,119,125 A | 10/1978 | Elkins |
| 4,131,549 A | 12/1978 | Ferrara |
| 4,134,832 A | 1/1979 | Heimreid |
| 4,142,668 A | 3/1979 | Lee |
| 4,152,270 A | 5/1979 | Cornell |
| 4,154,690 A | 5/1979 | Ballies |
| 4,159,896 A | 7/1979 | Levine et al. |
| 4,169,060 A | 9/1979 | Columbus |
| 4,189,385 A | 2/1980 | Greenspan |
| 4,201,209 A | 5/1980 | LeVeen et al. |
| 4,202,769 A | 5/1980 | Greenspan |
| 4,243,362 A | 1/1981 | Rees et al. |
| 4,246,123 A | 1/1981 | Cornell et al. |
| 4,257,886 A | 3/1981 | Kessler |
| 4,275,030 A | 6/1981 | Mares |
| 4,279,863 A | 7/1981 | Friehler |
| 4,294,707 A | 10/1981 | Ikeda et al. |
| 4,315,892 A | 2/1982 | Stone et al. |
| 4,364,832 A | 12/1982 | Ballies |
| 4,369,117 A | 1/1983 | White |
| 4,379,849 A | 4/1983 | Heimreid |
| 4,381,275 A | 4/1983 | Sorensen |
| 4,396,381 A | 8/1983 | Fanger et al. |
| 4,409,988 A | 10/1983 | Greenspan |
| 4,417,981 A | 11/1983 | Nugent |
| 4,425,235 A | 1/1984 | Cornell et al. |
| 4,426,290 A | 1/1984 | Ichikawa et al. |
| 4,443,345 A | 4/1984 | Wells |
| 4,444,711 A | 4/1984 | Schad |
| 4,448,741 A | 5/1984 | Schad |
| 4,464,254 A | 8/1984 | Dojki et al. |
| 4,470,936 A | 9/1984 | Potter |
| 4,492,634 A | 1/1985 | Villa-Real |
| 4,508,676 A | 4/1985 | Sorensen |
| 4,517,090 A | 5/1985 | Kersten et al. |
| 4,522,713 A | 6/1985 | Nussbaumer et al. |
| 4,533,474 A | 8/1985 | Arnaudeau |
| 4,535,014 A | 8/1985 | Wright |
| 4,567,754 A | 2/1986 | Wardlaw et al. |
| 4,569,764 A | 2/1986 | Satchell |
| 4,602,995 A | 7/1986 | Cassaday et al. |
| 4,701,292 A | 10/1987 | Valyi |
| 4,707,276 A | 11/1987 | Dodge et al. |
| 4,717,324 A | 1/1988 | Schad et al. |
| 4,726,758 A | 2/1988 | Sekine et al. |
| 4,770,779 A | 9/1988 | Ichikawa et al. |
| 4,803,031 A | 2/1989 | Ochs et al. |
| 4,818,386 A | 4/1989 | Burns |
| 4,828,716 A | 5/1989 | McEwen et al. |
| 4,832,851 A | 5/1989 | Bowers et al. |
| 4,853,137 A | 8/1989 | Ersson |
| 4,877,520 A | 10/1989 | Burns |
| 4,917,801 A | 4/1990 | Luderer et al. |
| 4,935,184 A | 6/1990 | Sorensen |
| 4,957,637 A | 9/1990 | Cornell |
| 4,957,682 A | 9/1990 | Kobayashi et al. |
| 5,007,892 A | 4/1991 | Columbus |
| 5,019,243 A | 5/1991 | McEwen et al. |
| 5,028,226 A | 7/1991 | De'ath et al. |
| 5,030,341 A | 7/1991 | McEwen et al. |
| 5,086,784 A | 2/1992 | Levine et al. |
| 5,112,490 A | 5/1992 | Turpen |
| 5,171,533 A | 12/1992 | Fine et al. |
| 5,236,604 A | 8/1993 | Fiehler |
| 5,251,474 A | 10/1993 | Wardlaw et al. |
| 5,269,927 A | 12/1993 | Fiehler |
| 5,271,852 A | 12/1993 | Luoma, II |
| 5,282,981 A | 2/1994 | Adams et al. |
| 5,308,506 A | 5/1994 | McEwen et al. |
| 5,325,977 A | 7/1994 | Haynes et al. |
| 5,354,483 A | 10/1994 | Furse |
| 5,389,265 A | 2/1995 | Luoma, II |
| 5,393,494 A | 2/1995 | Greenfield et al. |
| 5,419,835 A | 5/1995 | Adams et al. |
| 5,422,018 A | 6/1995 | Saunders et al. |
| 5,454,958 A | 10/1995 | Fiehler |
| 5,455,009 A | 10/1995 | Vogler et al. |
| 5,456,885 A | 10/1995 | Coleman et al. |
| 5,462,716 A | 10/1995 | Holm |
| 5,474,687 A | 12/1995 | Van Vlasselaer |
| 5,511,558 A | 4/1996 | Shepard et al. |
| 5,533,518 A | 7/1996 | Vogler |
| 5,552,325 A | 9/1996 | Nochumson et al. |
| 5,556,541 A | 9/1996 | Ruschke |
| 5,560,830 A | 10/1996 | Coleman et al. |
| 5,575,778 A | 11/1996 | Hardt et al. |
| 5,577,513 A | 11/1996 | Van Vlasselaer |
| 5,632,895 A | 5/1997 | Tsukagoshi et al. |
| 5,632,905 A | 5/1997 | Haynes |

(56) References Cited

U.S. PATENT DOCUMENTS

| | | |
|---|---|---|
| 5,646,004 A | 7/1997 | Van Vlasselaer |
| 5,648,223 A | 7/1997 | Van Vlasselaer |
| 5,651,998 A | 7/1997 | Bertschi et al. |
| 5,707,876 A | 1/1998 | Levine |
| 5,736,033 A | 4/1998 | Coleman et al. |
| 5,755,360 A | 5/1998 | Elliott |
| 5,785,925 A | 7/1998 | U'Ren |
| 5,789,033 A | 8/1998 | Bertschi et al. |
| 5,798,069 A | 8/1998 | Bertschi et al. |
| 5,840,502 A | 11/1998 | Van Vlasselaer |
| 5,853,600 A | 12/1998 | McNeal et al. |
| 5,860,937 A | 1/1999 | Cohen |
| 5,902,276 A | 5/1999 | Namey, Jr. |
| 5,955,009 A | 9/1999 | Kazuma |
| 6,001,087 A | 12/1999 | Zurcher |
| 6,074,613 A | 6/2000 | Harness et al. |
| 6,074,883 A | 6/2000 | Kelly et al. |
| 6,106,261 A | 8/2000 | von Holdt |
| 6,161,712 A | 12/2000 | Savitz et al. |
| 6,174,447 B1 | 1/2001 | Spindler |
| 6,225,123 B1 | 5/2001 | Cohen et al. |
| 6,277,331 B1 | 8/2001 | Konrad |
| 6,280,400 B1 | 8/2001 | Niermann |
| 6,296,796 B1 | 10/2001 | Gordon |
| 6,302,919 B1 | 10/2001 | Chambers et al. |
| 6,379,139 B1 | 4/2002 | Boucherie |
| 6,390,966 B2 | 5/2002 | Anderson |
| 6,406,671 B1 | 6/2002 | DiCesare et al. |
| 6,409,528 B1 | 6/2002 | Bodnar |
| 6,464,921 B1 | 10/2002 | Armbruster |
| 6,465,256 B1 | 10/2002 | Iskra |
| 6,471,069 B2 | 10/2002 | Lin et al. |
| 6,479,298 B1 | 11/2002 | Miller et al. |
| 6,497,325 B1 | 12/2002 | DiCesare et al. |
| 6,516,953 B1 | 2/2003 | DiCesare et al. |
| 6,537,503 B1 | 3/2003 | Conway |
| 6,558,149 B1 | 5/2003 | Bodmer et al. |
| 6,582,904 B2 | 6/2003 | Dahm |
| 6,593,145 B2 | 7/2003 | Macfarlane et al. |
| 6,607,685 B2 | 8/2003 | Naritomi et al. |
| 6,623,688 B2 | 9/2003 | Gedritis et al. |
| 6,740,240 B2 | 5/2004 | Coville et al. |
| 6,758,804 B2 | 7/2004 | Anderson |
| 6,783,346 B2 | 8/2004 | Bodmer et al. |
| 6,793,892 B1 | 9/2004 | Niermann |
| 6,803,022 B2 | 10/2004 | DiCesare et al. |
| 6,817,256 B2 | 11/2004 | Mehra et al. |
| 6,866,811 B2 | 3/2005 | Kayano et al. |
| 6,933,148 B2 | 8/2005 | Collins et al. |
| 6,976,509 B1 | 12/2005 | Kirvan |
| 6,979,307 B2 | 12/2005 | Beretta et al. |
| 7,074,577 B2 | 7/2006 | Haubert et al. |
| 7,077,273 B2 | 7/2006 | Ellsworth et al. |
| 7,153,477 B2 | 12/2006 | DiCesare et al. |
| 7,158,854 B1 | 1/2007 | Kolander |
| 7,166,218 B2 | 1/2007 | Trapy et al. |
| 7,179,391 B2 | 2/2007 | Leach et al. |
| 7,188,734 B2 | 3/2007 | Konrad |
| 7,205,157 B2 | 4/2007 | Jurgensen et al. |
| 7,211,433 B1 | 5/2007 | Dahm et al |
| 7,220,593 B2 | 5/2007 | Haubert et al. |
| 7,223,346 B2 | 5/2007 | Dorian et al. |
| 7,282,168 B2 | 10/2007 | Downer et al. |
| 7,294,311 B2 | 11/2007 | Coville |
| 7,309,468 B2 | 12/2007 | Stevens et al. |
| 7,329,534 B2 | 2/2008 | Haubert et al. |
| 7,358,095 B2 | 4/2008 | Haubert et al. |
| 7,374,678 B2 | 5/2008 | Leach et al. |
| 7,445,125 B2 | 11/2008 | Ellsworth et al. |
| 7,470,371 B2 | 12/2008 | Dorian et al. |
| 7,547,272 B2 | 6/2009 | Ellsworth et al. |
| 7,578,975 B2 | 8/2009 | DiCesare et al. |
| 7,629,176 B2 | 12/2009 | Haubert et al. |
| 7,645,425 B2 | 1/2010 | Haywood et al. |
| 7,736,593 B2 | 6/2010 | Dastane et al. |
| 7,745,106 B2 | 6/2010 | Beretta et al. |
| 7,767,087 B2 | 8/2010 | Wilson |
| 7,771,590 B2 | 8/2010 | Leach et al. |
| 7,780,860 B2 | 8/2010 | Higgins et al. |
| 7,806,276 B2 | 10/2010 | Leach et al. |
| 7,832,566 B2 | 11/2010 | Leach et al. |
| 7,837,884 B2 | 11/2010 | Dorian et al. |
| 7,845,499 B2 | 12/2010 | Higgins et al. |
| 7,901,584 B2 | 3/2011 | Dorian et al. |
| 7,914,689 B2 | 3/2011 | Higgins et al. |
| 7,915,029 B2 | 3/2011 | Haubert et al. |
| 7,919,049 B2 | 4/2011 | Haubert et al. |
| 7,922,972 B2 | 4/2011 | Ellsworth et al. |
| 7,927,563 B1 | 4/2011 | Lavi |
| 7,947,186 B2 | 5/2011 | Soares et al. |
| 7,947,236 B2 | 5/2011 | Losada et al. |
| 7,954,646 B2 | 6/2011 | Leach et al. |
| 7,955,501 B2 | 6/2011 | Wilson |
| 7,972,578 B2 | 7/2011 | DiCesare et al. |
| 7,992,725 B2 | 8/2011 | Leach et al. |
| 8,012,077 B2 | 9/2011 | Hoeppner |
| 8,012,742 B2 | 9/2011 | Haubert et al. |
| 8,048,320 B2 | 11/2011 | Leach et al. |
| 8,048,321 B2 | 11/2011 | Leach et al. |
| 8,062,534 B2 | 11/2011 | Higgins et al. |
| 8,092,692 B2 | 1/2012 | Nilsen et al. |
| 8,114,680 B2 | 2/2012 | Haubert et al. |
| 8,119,013 B2 | 2/2012 | Leach et al. |
| 8,133,389 B2 | 3/2012 | Dorian et al. |
| RE43,547 E | 7/2012 | Ellsworth et al. |
| 8,282,839 B2 | 10/2012 | Ellsworth |
| 8,313,954 B2 | 11/2012 | Leach et al. |
| 8,348,066 B2 | 1/2013 | Ellsworth |
| 8,394,342 B2 | 3/2013 | Felix et al. |
| 8,474,630 B2 | 7/2013 | Dorian et al. |
| 2002/0023884 A1 | 2/2002 | Anderson |
| 2002/0094305 A1 | 7/2002 | DiCesare et al. |
| 2002/0098137 A1 | 7/2002 | Hommeltoft |
| 2002/0132367 A1 | 9/2002 | Miller et al. |
| 2002/0156439 A1 | 10/2002 | Iskra |
| 2002/0185778 A1 | 12/2002 | Armbruster |
| 2003/0028154 A1 | 2/2003 | Ross |
| 2003/0039717 A1 | 2/2003 | Hwang et al. |
| 2003/0205538 A1 | 11/2003 | Dorian et al. |
| 2004/0013575 A1 | 1/2004 | Stevens et al. |
| 2004/0043505 A1 | 3/2004 | Walenciak et al. |
| 2004/0059255 A1 | 3/2004 | Manoussakis et al. |
| 2004/0129631 A1 | 7/2004 | Anraku et al. |
| 2004/0149287 A1 | 8/2004 | Namey, Jr. |
| 2004/0166029 A1 | 8/2004 | Losada et al. |
| 2004/0210196 A1 | 10/2004 | Bush Jr et al. |
| 2004/0241364 A1 | 12/2004 | Zihlmann |
| 2004/0256331 A1 | 12/2004 | Arking et al. |
| 2005/0033237 A1 | 2/2005 | Fentress et al. |
| 2005/0037165 A1 | 2/2005 | Ahern et al. |
| 2005/0059163 A1 | 3/2005 | Dastane et al. |
| 2005/0124965 A1 | 6/2005 | Haywood |
| 2005/0170114 A1 | 8/2005 | Hill |
| 2005/0186120 A1 | 8/2005 | Dorian et al. |
| 2005/0261620 A1 | 11/2005 | Ballin |
| 2006/0032825 A1 | 2/2006 | Ellsworth et al. |
| 2006/0036231 A1 | 2/2006 | Conard et al. |
| 2006/0068206 A1 | 3/2006 | Hala et al. |
| 2006/0089602 A1 | 4/2006 | Boucherie |
| 2006/0116270 A1 | 6/2006 | Hatamian et al. |
| 2006/0212020 A1 | 9/2006 | Rainen et al. |
| 2006/0263266 A1 | 11/2006 | DiCesare et al. |
| 2006/0278588 A1 | 12/2006 | Woodell-May |
| 2007/0020629 A1 | 1/2007 | Ross et al. |
| 2007/0034579 A1 | 2/2007 | Dorian et al. |
| 2007/0096364 A1 | 5/2007 | Hahn et al. |
| 2007/0102344 A1 | 5/2007 | Konrad |
| 2007/0191775 A1 | 8/2007 | Diep et al. |
| 2007/0267776 A1 | 11/2007 | Conard et al. |
| 2008/0023414 A1 | 1/2008 | Konrad |
| 2008/0290048 A1 | 11/2008 | Jaeggi et al. |
| 2010/0120596 A1 | 5/2010 | Froman et al. |
| 2010/0155343 A1 | 6/2010 | Battles et al. |
| 2010/0160135 A1 | 6/2010 | Bartfeld et al. |

(56) References Cited

U.S. PATENT DOCUMENTS

| | | |
|---|---|---|
| 2010/0288694 A1 | 11/2010 | Crawford et al. |
| 2011/0014705 A1 | 1/2011 | Leach et al. |
| 2011/0100919 A1 | 5/2011 | Dorian et al. |
| 2011/0266206 A1 | 11/2011 | Coleman |
| 2012/0015796 A1 | 1/2012 | Leach et al. |
| 2012/0045424 A1 | 2/2012 | Esteron |
| 2012/0129676 A1 | 5/2012 | Duffy et al. |
| 2013/0017130 A1 | 1/2013 | Haubert |
| 2013/0095007 A1 | 4/2013 | Haubert et al. |

FOREIGN PATENT DOCUMENTS

| | | |
|---|---|---|
| DE | 19513453 C2 | 3/1997 |
| DE | 102010000645 A1 | 9/2011 |
| EP | 0017127 A2 | 10/1980 |
| EP | 0056609 A2 | 7/1982 |
| EP | 0119692 A2 | 9/1984 |
| EP | 0137292 B1 | 3/1990 |
| EP | 0392377 A2 | 10/1990 |
| EP | 0184274 B1 | 5/1992 |
| EP | 0385953 B1 | 4/1993 |
| EP | 0537507 A1 | 4/1993 |
| EP | 0399151 B1 | 8/1994 |
| EP | 0638804 A1 | 2/1995 |
| EP | 0520184 B1 | 1/1996 |
| EP | 0520185 B1 | 2/1996 |
| EP | 0638171 B1 | 6/1996 |
| EP | 0753741 A1 | 1/1997 |
| EP | 0494079 B1 | 3/1997 |
| EP | 0766973 A1 | 4/1997 |
| EP | 0493838 B1 | 5/1997 |
| EP | 0627261 B1 | 5/1998 |
| EP | 0640215 B1 | 11/1998 |
| EP | 0817680 B1 | 12/1999 |
| EP | 0678557 B1 | 6/2000 |
| EP | 1005910 A2 | 6/2000 |
| EP | 1016460 A2 | 7/2000 |
| EP | 0688606 B1 | 12/2000 |
| EP | 1106252 A2 | 6/2001 |
| EP | 0739229 B1 | 10/2001 |
| EP | 0744026 B1 | 11/2001 |
| EP | 1205250 A1 | 5/2002 |
| EP | 1221342 A2 | 7/2002 |
| EP | 0875757 B1 | 6/2003 |
| EP | 0928301 B1 | 1/2004 |
| EP | 1005909 B1 | 5/2004 |
| EP | 1107002 B1 | 8/2004 |
| EP | 1192996 B1 | 8/2004 |
| EP | 1106250 B1 | 4/2005 |
| EP | 1106251 B1 | 11/2005 |
| EP | 1106253 B1 | 11/2005 |
| EP | 1014088 B1 | 3/2006 |
| EP | 1006360 B1 | 5/2006 |
| EP | 1693109 A1 | 8/2006 |
| EP | 1189967 B1 | 3/2007 |
| EP | 1772191 A1 | 4/2007 |
| EP | 1509326 B1 | 6/2007 |
| EP | 1289618 B1 | 1/2008 |
| GB | 2293986 A | 4/1996 |
| JP | 5555259 A | 4/1980 |
| JP | 6423166 A | 1/1989 |
| JP | 1295164 A | 11/1989 |
| JP | 3270701 A | 12/1991 |
| JP | 7103969 A | 4/1995 |
| JP | 8201380 A | 8/1996 |
| JP | 9292393 A | 11/1997 |
| JP | 11314011 A | 11/1999 |
| JP | 200074910 A | 3/2000 |
| JP | 2000199760 A | 7/2000 |
| JP | 2003185653 A | 7/2003 |
| JP | 2007244925 A | 9/2007 |
| WO | 9322673 A1 | 11/1993 |
| WO | 9520675 A1 | 8/1995 |
| WO | 9605770 A1 | 2/1996 |
| WO | 9607097 A1 | 3/1996 |
| WO | 9609308 A1 | 3/1996 |
| WO | 9712679 A1 | 4/1997 |
| WO | 9851411 A2 | 11/1998 |
| WO | 0114850 A1 | 3/2001 |
| WO | 0181002 A1 | 11/2001 |
| WO | 0209840 A1 | 2/2002 |
| WO | 02073190 A1 | 9/2002 |
| WO | 03035888 A1 | 5/2003 |
| WO | 03099412 A1 | 12/2003 |
| WO | 2004030826 A2 | 4/2004 |
| WO | 2004031770 A1 | 4/2004 |
| WO | 2005014173 A1 | 2/2005 |
| WO | 2005080965 A1 | 9/2005 |
| WO | 2006104636 A1 | 10/2006 |
| WO | 2006121728 A2 | 11/2006 |
| WO | 2006135856 A2 | 12/2006 |
| WO | 2007000986 A1 | 1/2007 |
| WO | 2007095450 A2 | 8/2007 |
| WO | 2008038012 A1 | 4/2008 |
| WO | 2008049359 A1 | 5/2008 |
| WO | 2008097091 A1 | 8/2008 |
| WO | 2008114998 A1 | 9/2008 |
| WO | 2008127639 A1 | 10/2008 |
| WO | 2009021257 A1 | 2/2009 |
| WO | 2011069145 A2 | 6/2011 |
| WO | 2011126867 A1 | 10/2011 |
| WO | 2012003873 A1 | 1/2012 |

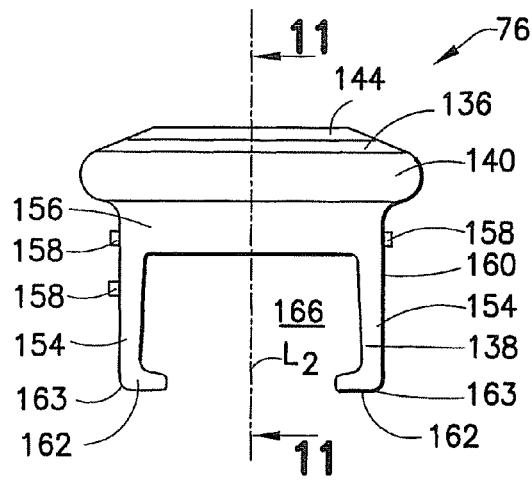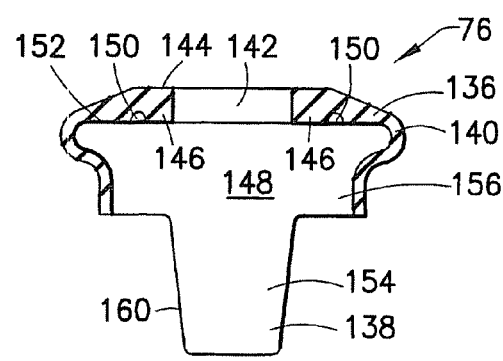
FIG.10  FIG.11
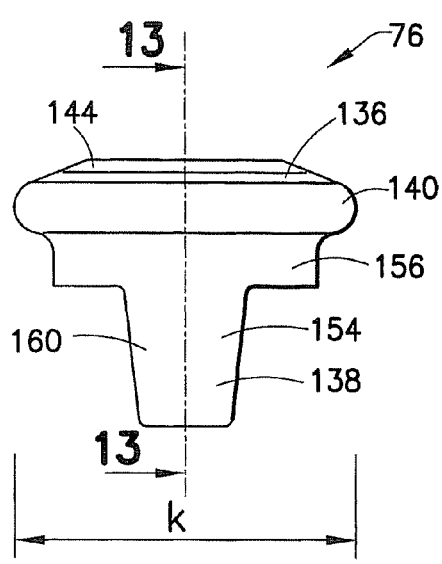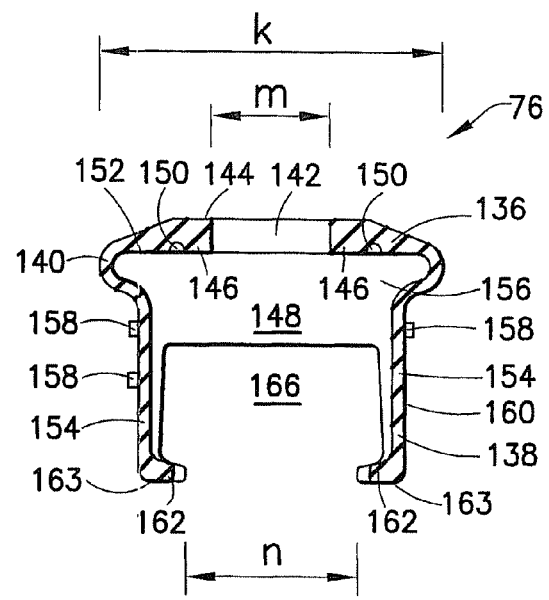
FIG.12  FIG.13

DENSITY PHASE SEPARATION DEVICE

CROSS REFERENCE TO RELATED APPLICATIONS

The present application is a continuation of U.S. Utility application Ser. No. 12/506,841, filed Jul. 21, 2009 which claims priority to U.S. Provisional Patent Application No. 61/082,361, filed Jul. 21, 2008, entitled "Density Phase Separation Device", the entire disclosures of each of which are hereby incorporated by reference.

BACKGROUND OF THE INVENTION

1. Field of the Invention

The subject invention relates to a device and method for separating heavier and lighter fractions of a fluid sample. More particularly, this invention relates to a device and method for collecting and transporting fluid samples whereby the device and fluid sample are subjected to centrifugation in order to cause separation of the heavier fraction from the lighter fraction of the fluid sample.

2. Description of Related Art

Diagnostic tests may require separation of a patient's whole blood sample into components, such as serum or plasma, (the lighter phase component), and red blood cells, (the heavier phase component). Samples of whole blood are typically collected by venipuncture through a cannula or needle attached to a syringe or an evacuated blood collection tube. After collection, separation of the blood into serum or plasma and red blood cells is accomplished by rotation of the syringe or tube in a centrifuge. In order to maintain the separation, a barrier must be positioned between the heavier and lighter phase components. This allows the separated components to be subsequently examined.

A variety of separation barriers have been used in collection devices to divide the area between the heavier and lighter phases of a fluid sample. The most widely used devices include thixotropic gel materials, such as polyester gels. However, current polyester gel serum separation tubes require special manufacturing equipment to both prepare the gel and fill the tubes. Moreover, the shelf-life of the product is limited. Over time, globules may be released from the gel mass and enter one or both of the separated phase components. These globules may clog the measuring instruments, such as the instrument probes used during the clinical examination of the sample collected in the tube. Furthermore, commercially available gel bathers may react chemically with the analytes. Accordingly, if certain drugs are present in the blood sample when it is taken, an adverse chemical reaction with the gel interface can occur.

Certain mechanical separators have also been proposed in which a mechanical barrier can be employed between the heavier and lighter phases of the fluid sample. Conventional mechanical barriers are positioned between heavier and lighter phase components utilizing differential buoyancy and elevated gravitational forces applied during centrifugation. For proper orientation with respect to plasma and serum specimens, conventional mechanical separators typically require that the mechanical separator be affixed to the underside of the tube closure in such a manner that blood fill occurs through or around the device when engaged with a blood collection set. This attachment is required to prevent the premature movement of the separator during shipment, handling and blood draw. Conventional mechanical separators are affixed to the tube closure by a mechanical interlock between the bellows component and the closure. Example devices are described in U.S. Pat. Nos. 6,803,022 and 6,479,298.

Conventional mechanical separators have some significant drawbacks. As shown in FIG. 1, conventional separators include a bellows 34 for providing a seal with the tube or syringe wall 38. Typically, at least a portion of the bellows 34 is housed within, or in contact with a closure 32. As shown in FIG. 1, as the needle 30 enters through the closure 32, the bellows 34 is depressed. This creates a void 36 in which blood may pool when the needle 30 is removed. This can result in needle clearance issues, sample pooling under the closure, device pre-launch in which the mechanical separator prematurely releases during blood collection, hemolysis, fibrin draping and/or poor sample quality. Furthermore, previous mechanical separators are costly and complicated to manufacture due to the complicated multi-part fabrication techniques.

Accordingly, a need exists for a separator device that is compatible with standard sampling equipment and reduces or eliminates the aforementioned problems of conventional separators. A need also exists for a separator device that is easily used to separate a blood sample, minimizes cross-contamination of the heavier and lighter phases of the sample during centrifugation, is independent of temperature during storage and shipping and is stable to radiation sterilization.

SUMMARY OF THE INVENTION

The present invention is directed to an assembly and method for separating a fluid sample into a higher specific gravity phase and a lower specific gravity phase. Desirably, the mechanical separator of the present invention may be used with a tube, and the mechanical separator is structured to move within the tube under the action of applied centrifugal force in order to separate the portions of a fluid sample. Most preferably, the tube is a specimen collection tube including an open end, a closed end or an apposing end, and a sidewall extending between the open end and closed end or apposing end. The sidewall includes an outer surface and an inner surface and the tube further includes a closure disposed to fit in the open end of the tube with a re-sealable septum. Alternatively, both ends of the tube may be open, and both ends of the tube may be sealed by elastomeric closures. At least one of the closures of the tube may include a needle pierceable re-sealable septum.

The mechanical separator may be disposed within the tube at a location between the top closure and the bottom of the tube. The separator includes opposed top and bottom ends and includes a float, a ballast, and a deformable bellows. The components of the separator are dimensioned and configured to achieve an overall density for the separator that lies between the densities of the phases of a fluid sample, such as a blood sample.

In one embodiment, the mechanical separator for separating a fluid sample into first and second phases within a tube includes a float having a first portion and a second portion, and a ballast circumferentially disposed about a section of the float and longitudinally moveable with respect to the float. The mechanical separator also includes a deformable bellows defining an open passageway extending between a first end and a second end. The ballast of the mechanical separator is engaged with the deformable bellows between the first end and the second end, and at least a portion of the float transitionable from a restraint position to a sealed position through the first end of the deformable bellows. The first portion of the float may be positioned within the interior of the deformable bellows in the restraint position, and the first portion of the float may be positioned at an exterior location longitudinally displaced from the deformable bellows in the sealed position. The float may have a first density, and the ballast may have a second density greater than the first density of the float.

The mechanical separator may be oriented such that the first portion of the float may be positioned below the first end of the deformable bellows in the restraint position, and the first portion of the float may be positioned above the first end of the deformable bellows in the sealed position. Transition of the float from the restraint position to the sealed position may occur as the float and ballast exert opposing forces on the deformable bellows allowing the float to be received within the deformable bellows. The float may include an engagement protrusion, and the deformable bellows may include a restraint shoulder. The engagement protrusion of the float may be releasably restrained within the deformable bellows by the restraint shoulder. In the sealed position, the float and the deformable bellows may form a liquid impermeable seal.

The float may also include a head portion and a body portion. The body portion of the float may include a first section having a first diameter and a second stepped section having a second diameter, the second diameter greater than the first diameter. The float may also be made of a solid material.

The ballast may include an interlock recess for accommodating a portion of the deformable bellows for attachment thereto. The ballast may also include an exterior surface and define an annular shoulder circumferentially disposed within the exterior surface.

Optionally, at least a portion of the first end of the deformable bellows may be structured for receipt within a closure. Further, at least a portion of the first end of the deformable bellows may be structured to receive a portion of the closure therein.

The float of the mechanical separator may be made of polypropylene, the ballast may be made of polyethylene terephthalate, and the deformable bellows may be made of a thermoplastic elastomer.

In another embodiment, a mechanical separator includes a float having a first portion and a second portion, and a ballast circumferentially disposed about a portion of the float and longitudinally moveable with respect to the float. The mechanical separator also includes a deformable bellows having an open first end and an open second end and defining an open passageway extending therebetween. The deformable bellows includes an exterior surface engaged with a portion of the ballast, and an interior surface releasably engaged with a portion of the float. The float may have a first density, and the ballast may have a second density greater than the first density of the float.

Optionally, at least a portion of the float is transitionable from a restraint position to a sealed position through the first end of the deformable bellows. The first portion of the float may be positioned within the interior of the deformable bellows in the restraint position, and the first portion of the float may be positioned at an exterior location longitudinally displaced from the deformable bellows in the sealed position. Transition of the float from the restraint position to the sealed position may occur as the float and ballast exert opposing forces on the deformable bellows allowing the float to be received within the deformable bellows. The mechanical separator may be oriented such that the first portion of the float may be positioned below the first end of the deformable bellows in the restraint position, and the first portion of the float may be positioned above the first end of the deformable bellows in the sealed position. In the sealed position, the float and the deformable bellows form a liquid impermeable seal. In one configuration, the float may include an engagement protrusion and the deformable bellows may include a restraint shoulder. The engagement protrusion of the float may be releasably restrained within the deformable bellows by the restraint shoulder.

In another embodiment, a separation assembly for enabling separation of a fluid sample into first and second phases, includes a tube having an open end, a closed end or an apposing end, and a sidewall extending therebetween. A closure adapted for sealing engagement with the open end of the tube is also included. The closure defines a recess, and a mechanical separator is releasably engaged within the recess. The mechanical separator includes a float having a first portion and a second portion, and a ballast circumferentially disposed about a section of the float and longitudinally moveable with respect to the float. The mechanical separator also includes a deformable bellows defining an open passageway extending between a first end and a second end. The ballast of the mechanical separator is engaged with the deformable bellows between the first end and the second end, and at least a portion of the float transitionable from a restraint position to a sealed position though the first end of the deformable bellows. The first portion of the float may be positioned within the interior of the deformable bellows in the restraint position, and the first portion of the float may be positioned at an exterior location longitudinally displaced from the deformable bellows in the sealed position. The float may have a first density, and the ballast may have a second density greater than the first density of the float.

The separation assembly may be oriented such that the first portion of the float may be positioned below the first end of the deformable bellows in the restraint position, and the first portion of the float may be positioned above the first end of the deformable bellows in the sealed position. Transition of the float from the restraint position to the sealed position may occur upon longitudinal deformation of the deformable bellows.

In yet another embodiment, a separation assembly for enabling separation of a fluid sample into first and second phases includes a tube, having an open end, a closed end or an apposing end, and a sidewall extending therebetween. A closure adapted for sealing engagement with the open end of the tube is also included. The closure defines a recess, and a mechanical separator is releasably engaged within the recess. The mechanical separator includes a float having a first portion and a second portion, and a ballast circumferentially disposed about a portion of the float and longitudinally moveable with respect to the float. The mechanical separator also includes a deformable bellows having an open first end and an open second end and defining an open passageway extending therebetween. The deformable bellows includes an exterior surface engaged with a portion of the ballast, and an interior surface releasably engaged with a portion of the float. The float may have a first density, and the ballast may have a second density greater than the first density of the float.

In one configuration, at least a portion of the float is transitionable from a restraint position to a sealed position through the first end of the deformable bellows. The first portion of the float may be positioned within the interior of the deformable bellows in the restraint position, and the first portion of the float may be positioned at an exterior location longitudinally displaced from the deformable bellows in the sealed position. Transition from the restraint position to the sealed position may occur upon longitudinal deformation of the deformable bellows.

In another embodiment, a method of separating a fluid sample into lighter and heavier phases within a tube includes the step of subjecting a separation assembly having a fluid sample disposed therein to accelerated rotational forces. The separation assembly includes a tube, having an open end, a closed end or an apposing end, and a sidewall extending therebetween. The separation assembly also includes a closure adapted for sealing engagement with the open end of the tube, with the closure defining a recess. The separation assembly further includes a mechanical separator releasably engaged within the recess. The mechanical separator includes a float having a first portion and a second portion, a ballast circumferentially disposed about a section of the float and longitudinally moveable with respect to the float, and a deformable bellows engaged with a portion of the sidewall. The deformable bellows defines an open passageway extending between a first end and a second end, with the ballast engaged with the deformable bellows between the first end and the second end. At least a portion of the float is transitionable from a restraint position to a sealed position through the first end of the deformable bellows. The method further includes the steps of disengaging the mechanical separator from the closure, and venting air from within the mechanical separator through the open passageway of the deformable bellows until the mechanical separator is submerged within the fluid. The method also includes the steps of elongating the deformable bellows to at least partially separate from the sidewall, and transitioning the float from the restraint position to the sealed position.

The assembly of the present invention is advantageous over existing separation products that utilize separation gel. In particular, the assembly of the present invention is more favorable than gel with regard to minimizing and does not interfere with analytes resulting from sample separation. Another attribute of the present invention is that the assembly of the present invention is more favorable than prior art with regard to minimizing interference with therapeutic drug monitoring analytes.

The assembly of the present invention is also advantageous over existing mechanical separators in that the deformable bellows of the mechanical separator is snapped over a boss that protrudes from the underside of the closure, which provides retention and launch load control. As such, the deformable bellows does not directly interface with the underside of the closure in the region where the needle exits the closure. Pre-launch is therefore minimized by eliminating the deformable bellows from the path of the collection needle. This further minimizes sample pooling under the closure, hemolysis, fibrin draping, and/or poor sample quality. Additionally, the assembly of the present invention does not require complicated extrusion techniques during fabrication and may employ two-shot molding techniques.

In accordance with yet another embodiment of the present invention, a separation assembly for enabling separation of a fluid sample into first and second phases includes a tube having an open end, an apposing end, and a sidewall extending therebetween. The separation assembly also includes a closure adapted for sealing engagement with the open end of the tube and a mechanical separator disposed within the tube. The mechanical separator includes a float having a first portion and a second portion, with the float having a first density. The mechanical separator also includes a ballast disposed about a portion of the float and longitudinally moveable with respect to the float, with the ballast having a second density greater than the first density of the float. The mechanical separator further includes a deformable bellows interfaced with the float, with the bellows having an open first end and an open second end and defining an open passageway extending therebetween. The deformable bellows includes an exterior surface engaged with a portion of the ballast, and an interior surface releasably engaged with a portion of the float, wherein centrifugal force is applied to the separation assembly when filled with fluid components of localized densities ranging from less than the density of the float and greater than the density of the ballast, and wherein sufficient centrifugal forces can seat the bellows onto the float.

Further details and advantages of the invention will become clear from the following detailed description when read in conjunction with the accompanying drawings.

BRIEF DESCRIPTION OF THE DRAWINGS

FIG. 10 is a front view of the deformable bellows of FIG. 2.

FIG. 11 is a cross-sectional view of the deformable bellows of FIG. 2 taken along line 11-11 of FIG. 10.

FIG. 12 is a side view of the deformable bellows of FIG. 2.

FIG. 13 is a cross-sectional view of the deformable bellows of FIG. 2 taken along line 13-13 of FIG. 12.

DESCRIPTION OF THE PREFERRED EMBODIMENTS

Figure 1:
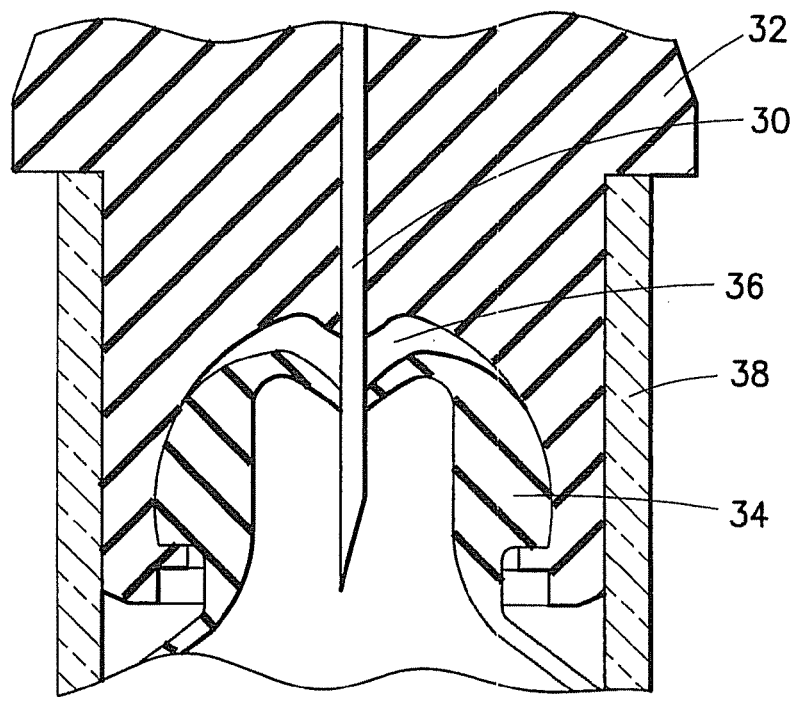
FIG. 1 is a partial cross-sectional side view of a conventional mechanical separator.

For purposes of the description hereinafter, the words "upper", "lower", "right", "left", "vertical", "horizontal", "top", "bottom", "lateral", "longitudinal" and like spatial terms, if used, shall relate to the described embodiments as oriented in the drawing figures. However, it is to be understood that many alternative variations and embodiments may be assumed except where expressly specified to the contrary. It is also to be understood that the specific devices and embodiments illustrated in the accompanying drawings and described herein are simply exemplary embodiments of the invention.

Figure 2:
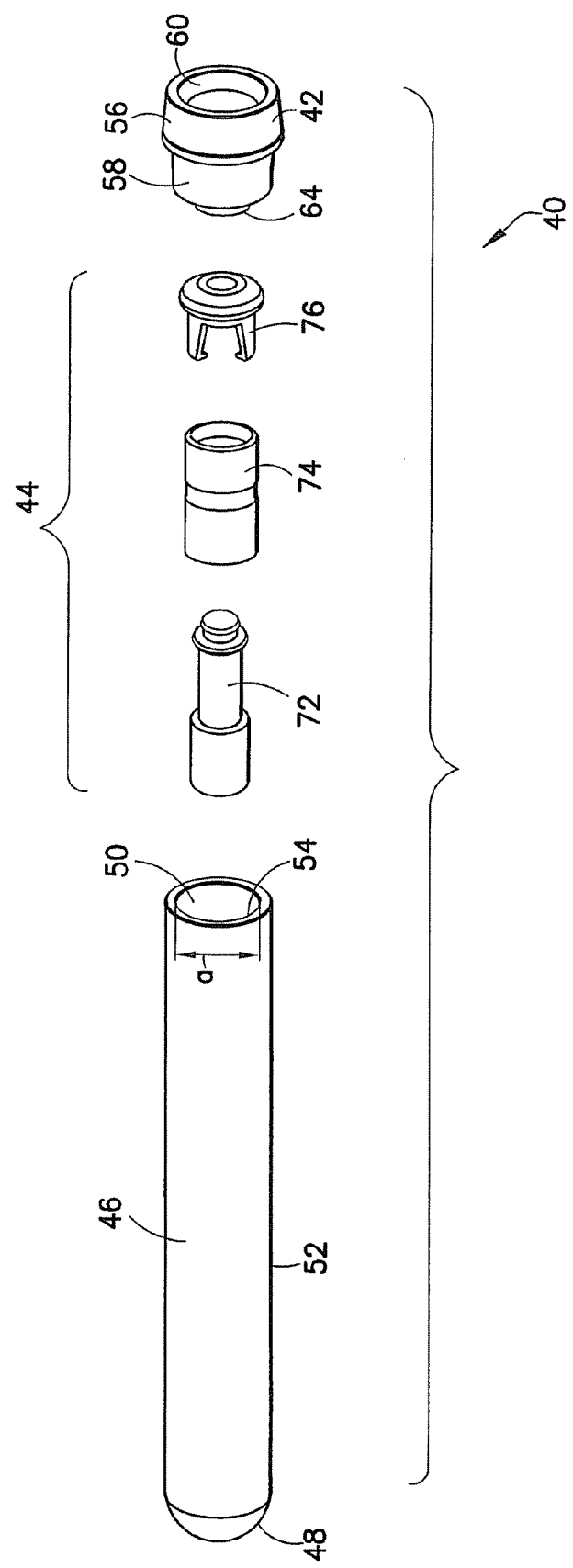
FIG. 2 is an exploded perspective view of a mechanical separation assembly including a closure, a deformable bellows, a ballast, a float, and a collection tube in accordance with an embodiment of the present invention.

As shown in exploded perspective view in FIG. 2, the mechanical separation assembly 40 of the present invention includes a closure 42 with a mechanical separator 44, for use in connection with a tube 46 for separating a fluid sample into first and second phases within the tube 46. The tube 46 may be a sample collection tube, such as a proteomics, molecular diagnostics, chemistry sample tube, blood or other bodily fluid collection tube, coagulation sample tube, hematology sample tube, and the like. The tube 46 may also contain additional additives as required for a particular tube function. For example, the tube 46 may contain a clot inhibiting agent, clotting agents, and the like. These additives may be provided in particle or liquid form and may be sprayed onto the tube 46 or located at the bottom of the tube 46. Desirably, tube 46 is an evacuated blood collection tube. The tube 46 may include a closed or an apposing bottom end 48, an open top end 50, and a cylindrical sidewall 52 extending therebetween. The cylindrical sidewall 52 includes an inner surface 54 with an inside diameter "a" extending substantially uniformly from the open top end 50 to a location substantially adjacent the closed bottom end 48.

The tube 46 may be made of one or more than one of the following representative materials: polypropylene, polyethylene terephthalate (PET), glass, or combinations thereof. The tube 46 can include a single wall or multiple wall configurations. Additionally, the tube 46 may be constructed in any practical size for obtaining an appropriate biological sample. For example, the tube 46 may be of a size similar to conventional large volume tubes, small volume tubes, or microtainer tubes, as is known in the art. In one particular embodiment, the tube 46 may be a standard 3 ml evacuated blood collection tube, or an 8.5 ml blood draw tube having a 16 mm diameter and a length of 100 mm, as is also known in the art.

The open top end 50 is structured to at least partially receive the closure 42 therein to form a liquid impermeable seal. The closure includes a top end 56 and a bottom end 58 structured to be at least partially received within the tube 46. Portions of the closure 42 adjacent the top end 56 define a maximum outer diameter which exceeds the inside diameter "a" of the tube 46.

Figure 3:
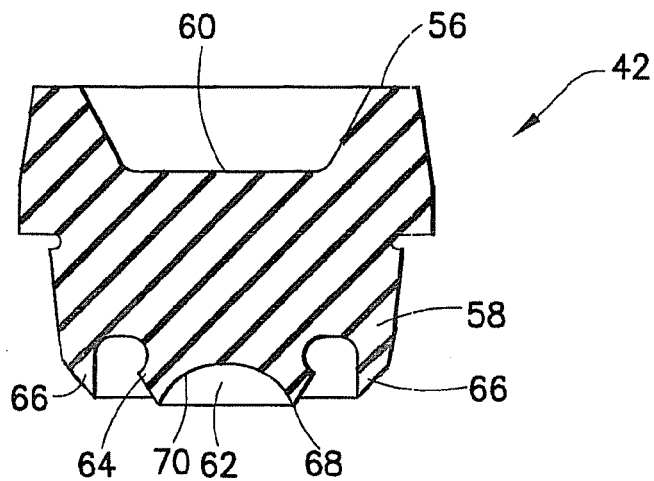
FIG. 3 is a cross-sectional front view of the closure of FIG. 2.

As shown in FIGS. 2-3, portions of the closure 42 at the top end 56 include a central recess 60 which define a pierceable re-sealable septum. Portions of the closure 42 extending downwardly from the bottom end 58 may taper from a minor diameter which is approximately equal to, or slightly less than, the inside diameter "a" of the tube 46 to a major diameter that is greater than the inside diameter "a" of the tube 46. Thus, the bottom end 58 of the closure 42 may be urged into a portion of the tube 46 adjacent the open top end 50. The inherent resiliency of closure 42 can insure a sealing engagement with the inner surface of the cylindrical sidewall 52 of the tube 46.

In one embodiment, the closure 42 can be formed of a unitarily molded rubber or elastomeric material, having any suitable size and dimensions to provide sealing engagement with the tube 46. The closure 42 can also be formed to define a bottom recess 62 extending into the bottom end 58. The bottom recess 62 may be sized to receive at least a portion of the mechanical separator 44. In one embodiment, the bottom end 58 of the closure 42 includes a graduated boss portion 64, which extends from the bottom end 58 of the closure 42 for engagement with the mechanical separator 44. The graduated boss portion 64 of the closure may include an outer ridge 68 and an inner surface 70 disposed within the outer ridge 68. In one embodiment, the boss portion 64 may extend into a portion of the mechanical separator 44. Additionally, a plurality of spaced apart arcuate flanges 66 may extend around the bottom recess 62 to at least partially restrain the mechanical separator 44 therein. In one embodiment, the flanges 66 are continuous about the circumference of the bottom recess 62.

Optionally, the closure 42 may be at least partially surrounded by a shield, such as a Hemogard® Shield commercially available from Becton, Dickinson and Company, to shield the user from droplets of blood in the closure 42 and from potential blood aerosolisation effects when the closure 42 is removed from the tube 46, as is known.

Referring again to FIG. 2, the mechanical separator 44 includes a float 72, a ballast 74, and a deformable bellows 76 such that the ballast 74 is engaged with a portion of the deformable bellows 76 and the float 72 is also engaged with a portion of the deformable bellows 76.

Figure 4:
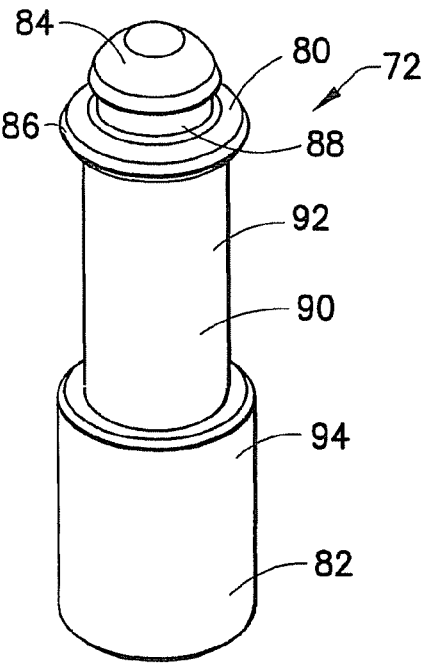
FIG. 4 is a perspective view of the float of FIG. 2.
Figure 5:
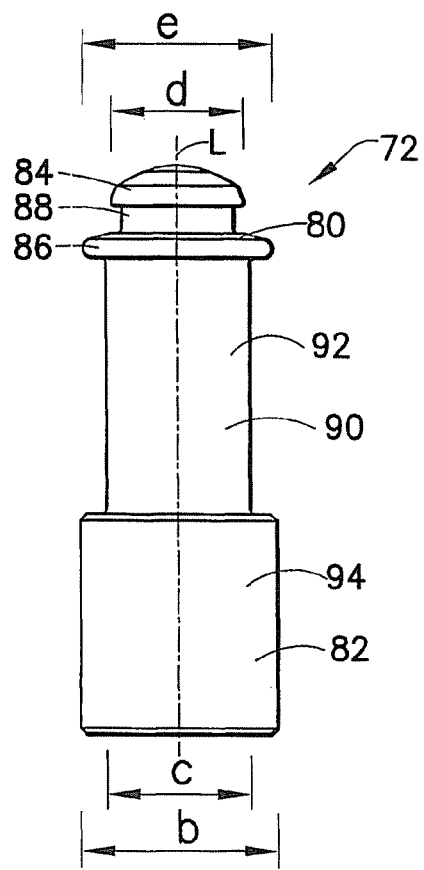
FIG. 5 is a front view of the float of FIG. 2.
Figure 6:
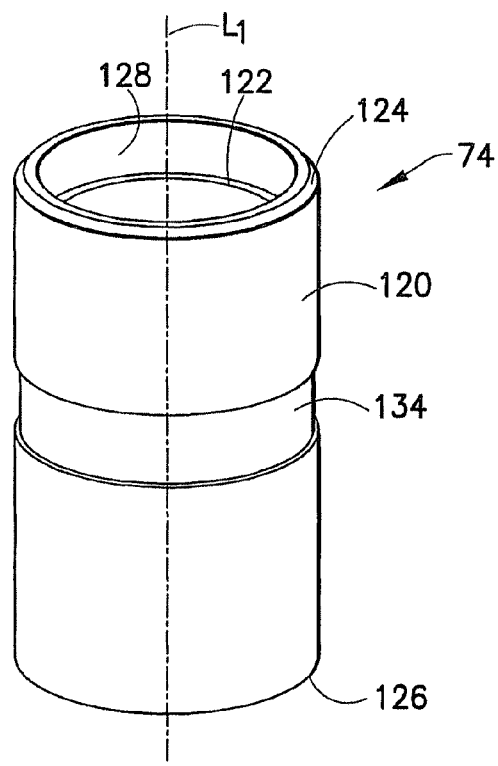
FIG. 6 is a perspective view of the ballast of FIG. 2.

Referring to FIGS. 4-5, the float 72 of the mechanical separator is a generally tubular body having an upper end 80 and a lower end 82. The upper end 80 of the float 72 may include a head portion 84 separated from the lower end 82 by an engagement protrusion 86. In one embodiment, the head portion 84 is separated from the engagement protrusion 86 by a neck portion 88. The lower end 82 of the float 72 may include a body portion 90 having a first section 92 and a second stepped section 94 graduated from the first section 92.

In one embodiment, the outer diameter "b" of the second stepped section 94 is less than the inside diameter "a" of the tube 46, shown in FIG. 2. In another embodiment, the outer diameter "c" of the first section 92 is less than the outer diameter "b" of the second stepped section 94. The outer diameter "d" of the head portion 84 is typically less than the outer diameter "c" of the first section 92 or the outer diameter "b" of the second stepped section 94. The outer diameter "e" of the engagement protrusion 86 is greater than the outer diameter "d" of the head portion 84. In one embodiment, the outer diameter "e" of the engagement protrusion 86 is less than the outer diameter "b" of the second stepped section 94. In another embodiment, the outer diameter "b" and the outer diameter "e" are the same size.

In one embodiment, the head portion 84 has a generally curved shape, such as having a curvature substantially corresponding to the curvature of the boss portion 64, shown in FIG. 3. In another embodiment, the head portion 84 has a curvature substantially corresponding to the curvature of the inner surface 70 of the boss portion 64, also shown in FIG. 3. The curvature of the head portion 84 may facilitate shedding of cells or other biological material during centrifugation.

The float 72 can be substantially symmetrical about a longitudinal axis L. In one embodiment, it is desirable that the float 72 of the mechanical separator 44 be made from a material having a density lighter than the liquid intended to be separated into two phases. For example, if it is desired to separate human blood into serum and plasma, then it is desirable that the float 72 have a density of no more than about 0.902 gm/cc. In one embodiment, the float 72 can be made of a solid material, such as polypropylene.

As shown in FIGS. 6-9, the ballast 74 of the mechanical separator 44 includes an upper end 124 and a lower end 126 with a generally cylindrical section 120 extending therebetween. In one embodiment, the ballast 74 includes an interior surface 122 structured to engage at least a portion of the deformable bellows 76, shown in FIG. 2. In another embodiment, the upper end 124 includes a recess 128 for receiving a portion of the deformable bellows 76, also shown in FIG. 2, therein.

The outer diameter "j" of the ballast 74 is less than the inside diameter "a" of the tube 46, shown in FIG. 2, therefore, the ballast 74 may freely slide within the tube 46. The inside diameter "i" of the recess 128 is less than the outer diameter "j" of the ballast 74, and can have any dimensions suitable to receive a portion of the deformable bellows 76, also shown in FIG. 2. The inner diameter "k" of the interior surface 122 of the ballast 74 is also greater than the outer diameter "b" of the second stepped section 94 of the float 72, shown in FIGS. 4-5.

Accordingly, the float 72 may freely move within the interior of the ballast 74. In one embodiment, the ballast is circumferentially disposed about at least a portion of the float 72. In yet another embodiment, the ballast 74 is longitudinally moveable with respect to the float 72.

Figure 7:
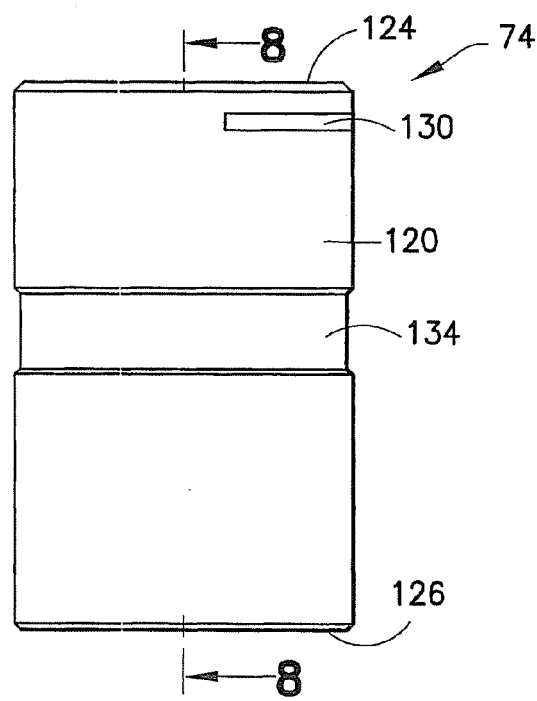
FIG. 7 is a front view of the ballast of FIG. 2.
Figure 8:
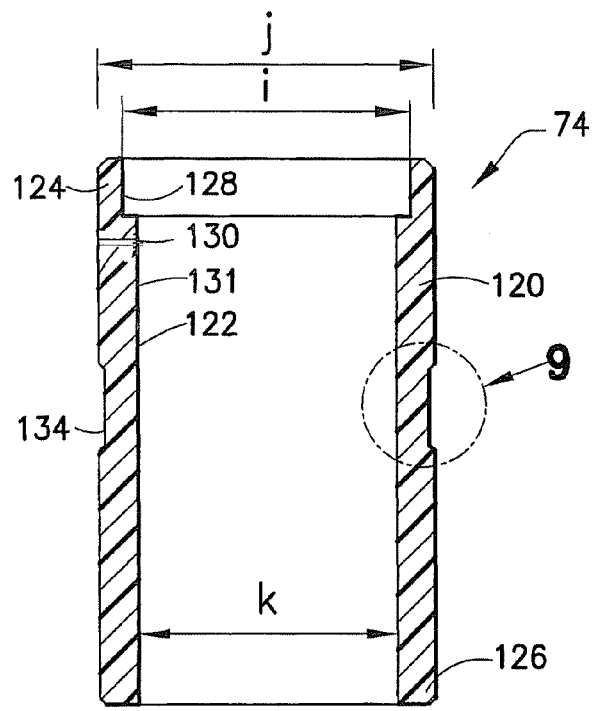
FIG. 8 is a cross-sectional view of the ballast of FIG. 2 taken along line 8-8 of FIG. 7.
Figure 9:
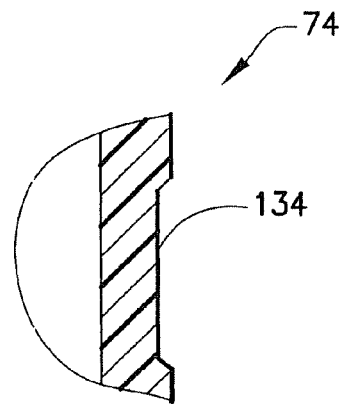
FIG. 9 is a close-up cross-sectional view of the ballast of FIG. 2 taken along section IX of FIG. 8.

As shown in FIG. 7, in one embodiment, the ballast 72 may include a mechanical interlock recess 130 extending through the generally cylindrical section 120, such as adjacent the upper end 124. In another embodiment, the ballast 72 may include the mechanical interlock recess 130 within an interior wall 131 for engagement with a portion of the deformable bellows 76, such as for accommodating a portion of the deformable bellows 76 for attachment thereto. In a further embodiment, the interlock recess 130 is located in recess 128.

In one embodiment, it is desirable that the ballast 74 of the mechanical separator 44 be made from a material having a density heavier than the liquid intended to be separated into two phases. For example, if it is desired to separate human blood into serum and plasma, then it is desirable that the ballast 74 have a density of at least 1.326 gm/cc. In one embodiment, the ballast 74 may have a density that is greater than the density of the float 72, shown in FIGS. 4-5. In another embodiment, the ballast 74 can be formed from PET.

As shown in FIGS. 6-9, the exterior surface of the ballast 74 may define an annular recess 134 circumferentially disposed about a longitudinal axis $L_1$ of the ballast 72, and extending into the exterior surface of the cylindrical section 120. In this embodiment, the annular recess 134 is structured to allow for an automated assembly to engage the ballast 74 with the deformable bellows 76 and/or float 72, shown in FIG. 2.

As shown in FIGS. 10-13, the deformable bellows 76 of the mechanical separator 44 includes an upper first end 136 and a lower second end 138 with an open passageway 142 extending therebetween. The upper first end 136 includes a deformable sealing portion 140 circumferentially disposed about the open passageway 142 for providing sealing engagement with the cylindrical sidewall 52 of the tube 46, shown in FIG. 2. The deformable sealing portion 140 can be positioned substantially adjacent the upper surface 144 of the upper first end 136 of the deformable bellows 76. The deformable sealing portion 140 may have a generally toroidal shape having an outside diameter "k" which, in an unbiased position, slightly exceeds the inside diameter "a" of the tube 46, shown in FIG. 2. However, oppositely directed forces on the upper first end 136 and the lower second end 138 of the deformable bellows 76 will lengthen the deformable sealing portion 140, simultaneously reducing the outer diameter "k" to a dimension less than "a". Likewise, the open passageway 142 has an inner diameter "m" which, in an unbiased position, is smaller than the outer diameter "d" of the head portion 84 of the float 72, shown in FIG. 5. Oppositely directed forces on the upper first end 136 and the lower second end 138 of the deformable bellows 76 will increase the inner diameter "m" of the open passageway to a diameter exceeding the outer diameter "d" of the head portion 84 of the float 72, again shown in FIG. 5.

The deformable bellows 76, including the deformable sealing portion 140, is substantially symmetrical (with the possible exception of the placement of protrusions 160) about a longitudinal axis $L_2$, and can be made of any sufficiently elastomeric material sufficient to form a liquid impermeable seal with the cylindrical sidewall 52 of the tube 46, shown in FIG. 2. In one embodiment, the deformable bellows 76 is made of a thermoplastic elastomer, such as thermoplastic polypropylene and has an approximate dimensional thickness of from about 0.020 inch to about 0.050 inch. In another embodiment, the entire bellows structure 70 is made of thermoplastic elastomer.

In one embodiment, the upper first end 136 of the deformable bellows 76 includes an annular shoulder 146 extending into the interior 148 of the deformable bellows 76 adjacent the deformable sealing portion 140. In another embodiment, the annular shoulder 146 may be an interior surface 152 of the upper first end 136 of the deformable bellows 76. Preferably, the annular shoulder 146 is positioned longitudinally above at least a portion of the deformable sealing portion 140. Alternatively, the annular shoulder 146 may be an interior surface 152 of the upper portion of the deformable sealing portion 140. In one embodiment, the deformable bellows 76 includes a recess 150 extending at least partially into the interior surface 152 of the upper first end 136. The recess 150 may be circumferentially disposed about the open passageway 142, and may be a continuous recess or a partitioned recess. The recess 150 may reduce the spring constant of the deformable bellows 76, allowing the deformable bellows 76 to longitudinally deform with less applied force. In one embodiment, this may be accomplished by reducing the wall section of the deformable bellows 76 to create a hinge.

In addition, at least a portion of deformable bellows 76, such as the upper first end 136, can be structured for receipt within the closure 42, such as the bottom recess 62, also shown in FIGS. 2-3. In one embodiment, at least a portion of the deformable sealing portion 140 of the deformable bellows 76 is structured for receipt within the bottom recess 62 of the closure 42.

The lower second end 138 of the deformable bellows 76 includes opposed depending portions 154 extending longitudinally downward from the upper first end 136. In one embodiment, the opposed depending portions 154 are connected to a lower end ring 156 extending circumferentially about the open passageway 142 and below the deformable sealing portion 140. In one embodiment, the opposed depending portions 154 include at least one ballast interlock protrusion 158 extending from a portion of the exterior surface 160. The interlock protrusion 158 is engageable with the interlock recess 130 of the ballast 74, shown in FIGS. 6-9, to secure the ballast 74 to a portion of the deformable bellows 76 between the upper first end 136 and the lower second end 138. Optionally, the interlock recess 130 of the ballast 74 may extend completely through the opposing wall of the ballast 74. In one embodiment, the exterior surface 160 of the deformable bellows 76 is secured with the interior wall 131 of the ballast 74, shown in FIGS. 6-9. In one embodiment, two-shot molding techniques may be used to secure the deformable bellows 76 to the ballast 74.

The lower second end 138 of the deformable bellows 76 may also include a restraint shoulder 162 extending into the interior 148 of the deformable bellows 76. The restraint shoulder 162 may be positioned at the bottom end 163 of the opposed depending portions 154. In one embodiment, the interior 148 of the deformable bellows 76 is structured to releasably retain at least a portion of the float 72, shown in FIGS. 4-5, therein. In another embodiment, the restraint shoulder 162 is structured to restrain the engagement protrusions 86 of the float 72 thereagainst, and dimensioned to allow a portion of the float 72, such as the head portion 84 to pass into the interior 148 of the deformable bellows 76. The inner diameter "n" of the deformable bellows adjacent the lower second end 138, such as extending between the restraint shoulder 162, is dimensioned to be greater than the inner diameter "m" of the open passageway 142, but smaller than the outer diameter "e" of the engagement protrusion 86 of the float 72, shown in FIG. 5. Therefore, a portion of the float 72, such as the head portion 84, may be received and retained within the interior 148 of the deformable bellows 76.

Figure 15:
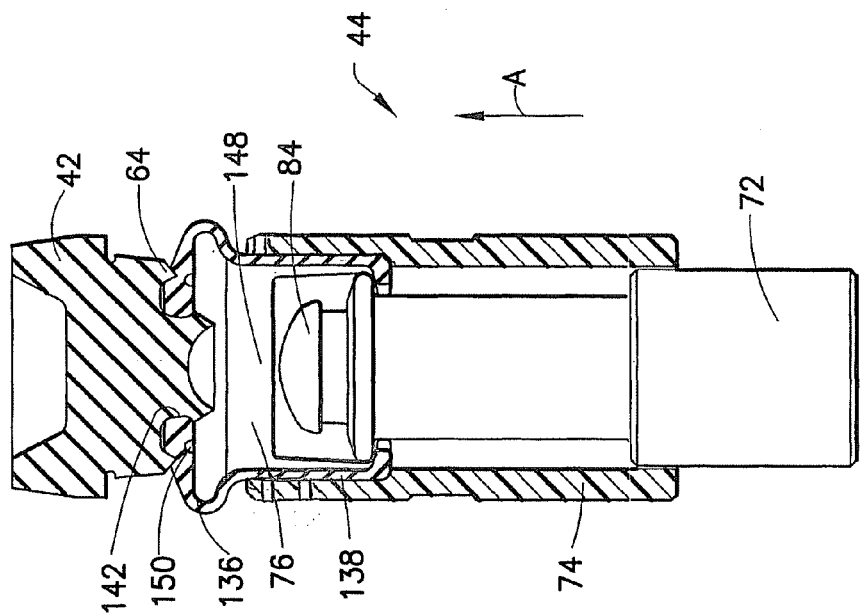
FIG. 15 is a cross-sectional view of the assembled mechanical separator engaged with the closure of FIG. 2 in the restraint position.
Figure 14:
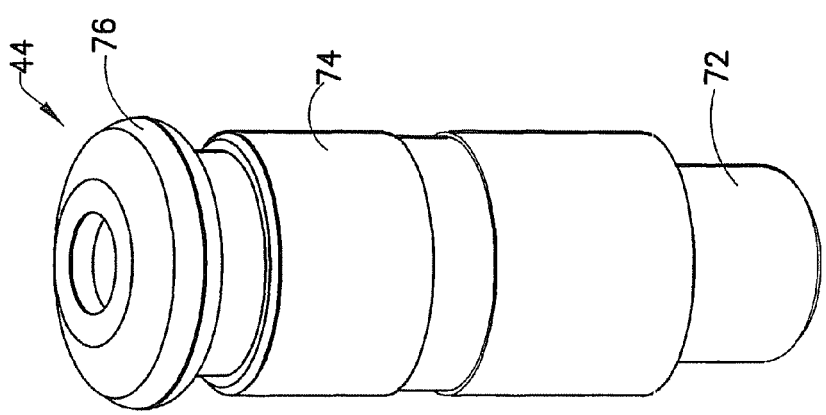
FIG. 14 is a perspective view of the assembled mechanical separator of FIG. 2 in the restraint position.

As shown in FIGS. 14-15, in the restraint position, the assembled mechanical separator 44 of the present invention includes a deformable bellows 76 engaged with the ballast 74. A portion of the float 72, such as the head portion 84, is engaged within the interior 148 of the deformable bellows 76. The float 72 may be secured at least partially within the interior 148 of the deformable bellows 76 by the mechanical engagement of the engagement protrusion 86 of the float 72 and the restraint shoulder 162 of the deformable bellows 76.

As shown in FIG. 15, the mechanical separator 44 can be engaged with a portion of the closure 42 in the restraint position. As shown, a portion of the closure 42, such as the boss portion 64, is received at least partially within the open passageway 142 of the deformable bellows 76. In one embodiment, the boss portion 64 is received within the open passageway 142 at the upper first end 136 of the deformable bellows 76 forming a liquid impermeable seal therewith.

A portion of the float 72, such as the head portion 84, may also be received within the open passageway 142 in the restraint position. In one embodiment, the head portion 84 of the float 72 is received within the open passageway 142 at the lower second end 138 of the deformable bellows 76. The float 72 is dimensioned such that the head portion 84, having an outer diameter "d", is greater than the inner diameter "m" of the open passageway 142 of the deformable bellows 76 at the upper first end 136, as shown in FIG. 13. Accordingly, the head portion 84 of the float 72 cannot pass through the open passageway 142 of the deformable bellows 76 in the restraint position.

Referring again to FIG. 15, the assembled mechanical separator 44 may be urged into the bottom recess 62 of the closure 42. This insertion engages the flanges 64 of the closure 42 with the upper first end 136 of the deformable bellows 76. During insertion, at least a portion of the upper first end 136 of the deformable bellows 76 will deform to accommodate the contours of the closure 42. In one embodiment, the closure 42 is not substantially deformed during insertion of the mechanical separator 44 into the bottom recess 62.

Figure 16:
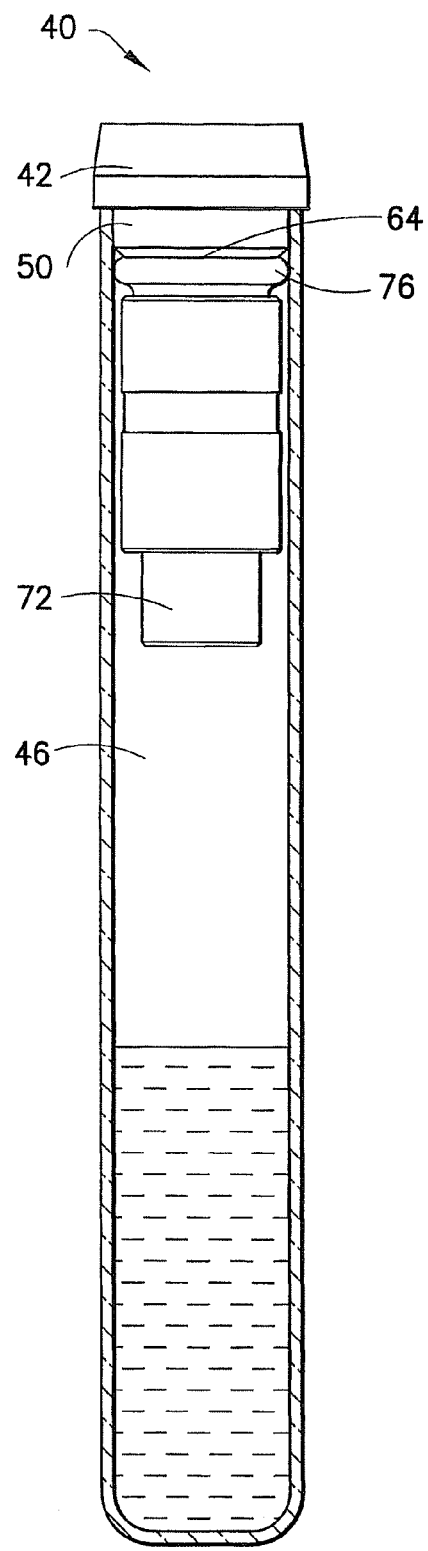
FIG. 16 is a front view of an assembly including a tube having a closure and a mechanical separator disposed therein in accordance with an embodiment of the present invention.
Figure 17:
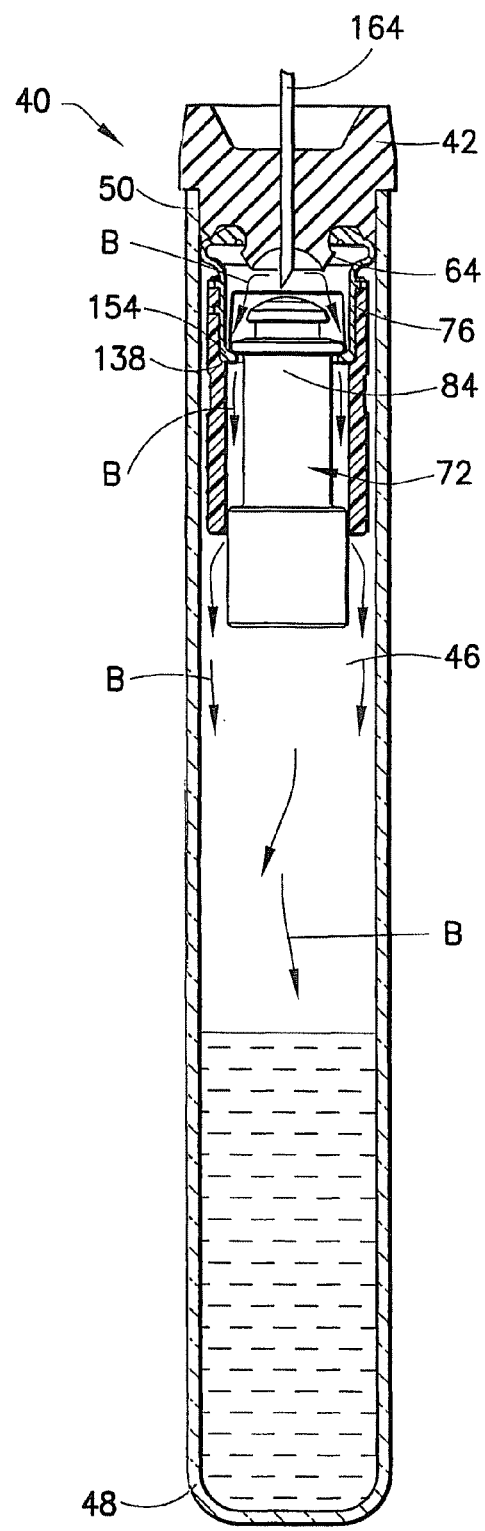
FIG. 17 is a cross-sectional front view of the assembly of FIG. 16 having a needle accessing the interior of the tube and an amount of fluid provided through the needle into the interior of the tube in accordance with an embodiment of the present invention.
Figure 18:
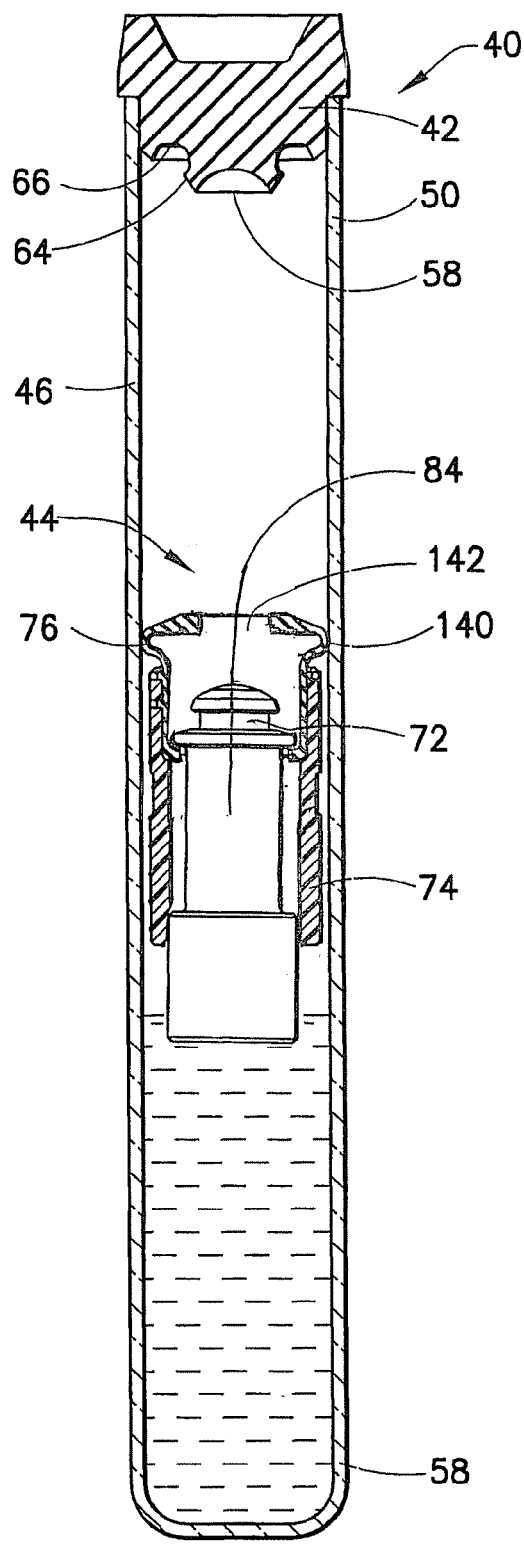
FIG. 18 is a cross-sectional front view of the assembly of FIG. 17 having the needle removed therefrom during use and the mechanical separator positioned apart from the closure in accordance with an embodiment of the present invention.

As shown in FIGS. 16-18, the mechanical separation assembly 40 includes a mechanical separator 44 and a closure 42 inserted into the open top end 50 of the tube 46, such that the mechanical separator 44 and the bottom end 58 of the closure 42 lie within the tube 46. The mechanical separator 44, including the deformable bellows 76, will sealingly engage the interior of the cylindrical sidewall 52 and the open top end of the tube 46.

As shown in FIG. 17, a liquid sample is delivered to the tube 46 by the puncture tip 164 that penetrates the septum of the top end 56 and the boss portion 64 of the closure 42. For purposes of illustration only, the liquid is blood. Blood will flow through the pierced boss portion 64 of the closure, through the open passageway 142 of the deformable bellows 76, shown in FIGS. 11 and 13, over the head portion 84 of the float 72, and through the space between the float 72 and the opposed depending portions 154 of the lower second end 138 of the deformable bellows 76. As shown in FIGS. 10 and 13, the opposed depending portions 154 define a fluid access area 166, therebetween to allow fluid received from the puncture tip 164 to pass between the float 72 and the deformable bellows 76 and into the closed bottom end 48 of the tube 46 as shown by the arrows B, reducing pre-launch of the mechanical separator.

As shown in FIG. 18, once a sufficient volume of fluid has been delivered to the tube 46, through the puncture tip 164 as above-described, the puncture tip 164 can be removed from the closure 42. In one embodiment, at least a portion of the closure 42, such as the boss portion 64, is made of a selfsealing material to form a liquid impermeable seal once the puncture tip 164 is removed. The mechanical separation assembly 40 may then be subjected to accelerated rotational forces, such as centrifuge, to separate the phases of the fluid.

Referring again to FIGS. 16-17, in use, the mechanical separator 44, particularly the deformable bellows 76, is intended to be restrained with the closure 42 until the mechanical separator 44 is subjected to accelerated rotational forces, such as within a centrifuge.

Figure 22:
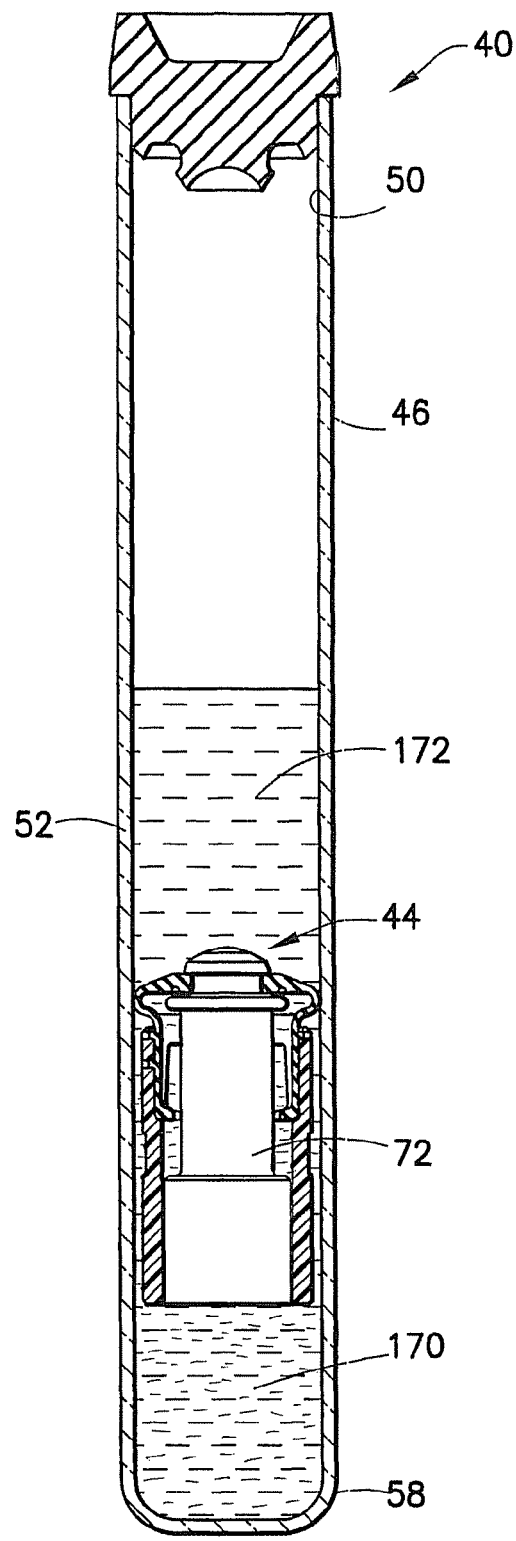
FIG. 22 is a cross-sectional front view of the assembly of FIG. 18 having the mechanical separator separating the less dense, portion of the fluid from the denser portion of the fluid in accordance with an embodiment of the present invention.

As shown in FIG. 18, upon application of accelerated rotational forces, such as centrifugation, the respective phases of the blood will begin to separate into a denser phase displaced toward the closed bottom end 58 of the tube 46, and a less dense phase displaced toward the top open end 50 of the tube 46, with the separated phases shown in FIG. 22. During centrifugation, the mechanical separator 44 experiences a force sufficient to disengage it from the closure 42. Once disengaged, the mechanical separator 44 travels down the tube 46 toward the fluid interface. Transition of the float 72 from the restraint position to the sealed position occurs as the mechanical separator 44 contacts and submerges in the fluid. As air trapped within the mechanical separator 44 vents through the open passageway 142 of the deformable bellows 76, the float 72 begins to move up within the mechanical separator 44 as soon as the mechanical separator 44 contacts the fluid interface and begins to submerge in the fluid. As the float 72 may be formed of a solid material, air is not trapped within the float 72 and thus, no additional venting mechanism is included within the float 72. As a result, leakage between the float 72 and the deformable bellows 76 is minimized.

Once the mechanical separator 44 is fully submerged, the float 72 and the ballast 74 exert opposing forces on the deformable bellows 76. As a result, the deformable bellows 76, and particularly the deformable sealing portion 140, become longer and narrower and become spaced concentrically inward from the inner surface of the cylindrical sidewall 52.

Referring to FIGS. 18-22, after the mechanical separator 44 has disengaged from the closure 42 and is submerged in the fluid, the outer diameter "n" (shown in FIG. 13) of the deformable sealing portion 140 is lessened, allowing the lighter phase components of the blood to slide past the deformable sealing portion 140 and travel upwards. Likewise, heavier phase components of the blood may slide past the deformable sealing portion 140 and travel downwards. As noted above, the mechanical separator 44 has an overall density between the densities of the separated phases of the blood. Upon application of applied centrifugal acceleration, the inner diameter "m" of the open passageway 142 of the deformable bellows 76 also deforms as a result of the opposing forces exerted upon it by the float 72 and the ballast 74. This deformation increases the inner diameter "m" of the open passageway 142, shown in FIG. 13, to a dimension greater than the outer diameter "d" of the head portion 84 of the float 72, shown in FIG. 5, thereby allowing the head portion 84 of the float 72 to pass through the open passageway 142. Accordingly, during centrifuge, the mechanical separator 44 is transitioned from a restraint position, shown in FIGS. 14-15, to a sealed position, shown in FIGS. 19-21.

Figure 19:
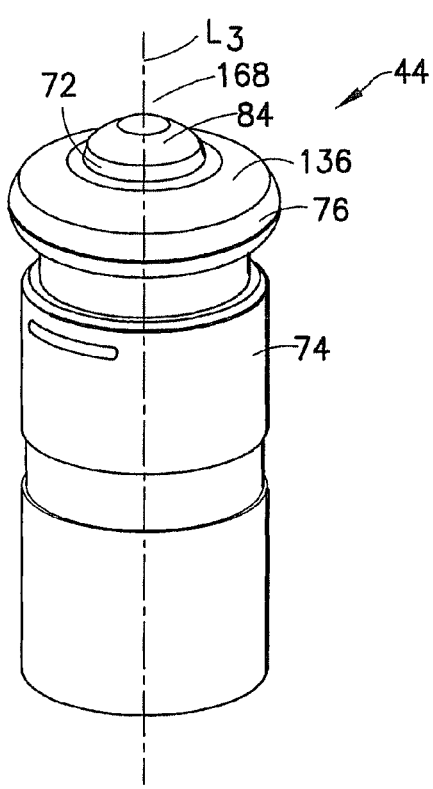
FIG. 19 is a perspective view of the assembled mechanical separator of FIG. 2 in the sealed position.
Figure 20:
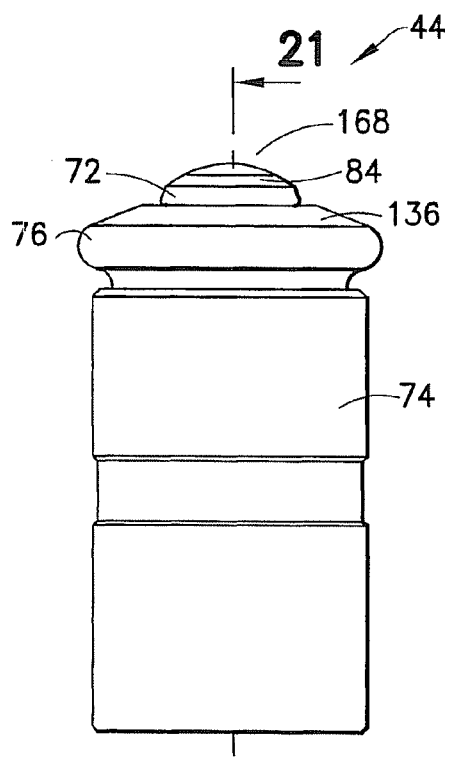
FIG. 20 is a front view of the assembled mechanical separator of FIG. 2 in the sealed position.
Figure 21:
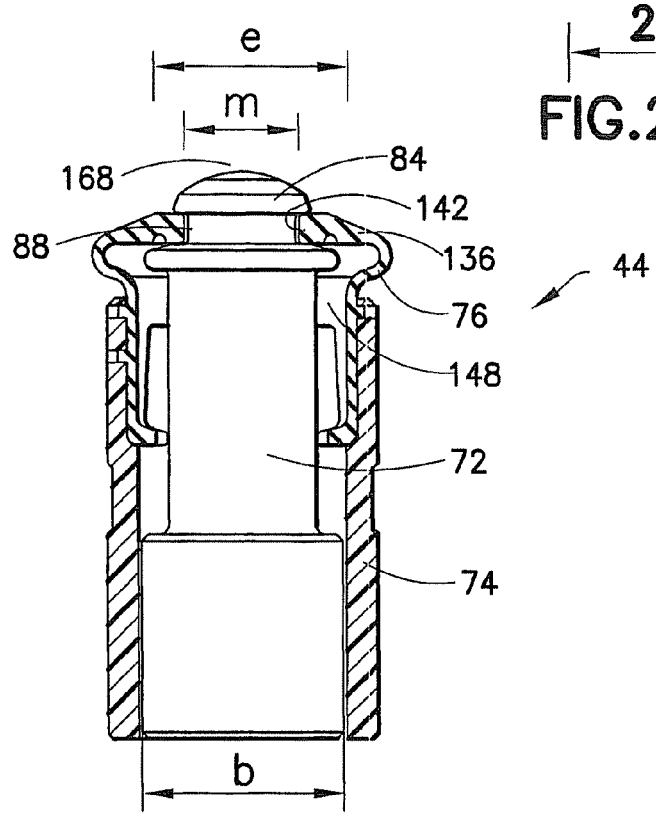
FIG. 21 is a cross-sectional view of the assembled mechanical separator of FIG. 2 in the sealed position taken along line 21-21 of FIG. 20.

Referring to FIGS. 19-21, the mechanical separator 44, including the deformable bellows 76, ballast 74, and float 72, is shown in the sealed position. As the inner diameter "m" of the open passageway 142 of the deformable bellows 76 of the mechanical separator 44 is increased during centrifuge, the head portion 84 of the float 72 may pass therethourgh. Preferably, the inner diameter "m" of the open passageway 142 of the deformable bellows 76 does not exceed the outer diameter "e" of the engagement protrusion 86 of the float 72 during deformation. Even more preferably, the inner diameter "m" of the open passageway 142 does not exceed the outer diameter "b" of the second stepped section 94 of the float 72 during deformation. Because the float 72 is made of a naturally buoyant material, the float 72 is urged upwardly as indicated by the arrow A.

Once centrifuge is ceased, the inner diameter "m" of the open passageway 142 returns to the unbiased position and engages the float 72 about the neck portion 88 in the sealed position. In one embodiment, the deformable bellows 76 form a liquid impermeable seal about the neck portion 88 of the float 72 through the open passageway 142 in the sealed position. In the sealed position, at least a portion of the float 72, such as the head portion 84, is positioned at a location exterior 168 to the deformable bellows 76, such as at a location exterior 168 to the interior 148 of the deformable bellows 76. In this embodiment, the head portion 84 may be positioned at an exterior location 168 that is longitudinally displaced from the deformable bellows 76 along the longitudinal axis $L_3$ of the mechanical separator 44 in the sealed position. Because the float 72 of the mechanical separator 44 is buoyant in fluid, when the mechanical separator 44 is oriented as shown in FIGS. 16-18, the head portion 84 of the float 72 may be positioned below the upper first end 136 of the deformable bellows 76, shown in FIG. 15, in the restraint position, and positioned above the upper first end 136 of the deformable bellows 76, shown in FIGS. 19-21, in the sealed position.

Referring to FIG. 22, after centrifuge and the transition of the mechanical separator 44 from the restraint position to the sealed position, the mechanical separator 44 will stabilize in a position within the tube 46 of the mechanical separation device 40, such that the heavier phase components 170 will be located between the mechanical separator 44 and the closed bottom end 58 of the tube 46, while the lighter phase components 172 will be located between the mechanical separator 44 and the top end of the tube 50. After this stabilized state has been reached, the centrifuge will be stopped and the deformable bellows 76, particularly the deformable sealing portion 140, will resiliently return to its unbiased state and into sealing engagement with the interior of the cylindrical sidewall 52 of the tube 46. The formed liquid phases may then be accessed separately for analysis.

Figure 23:
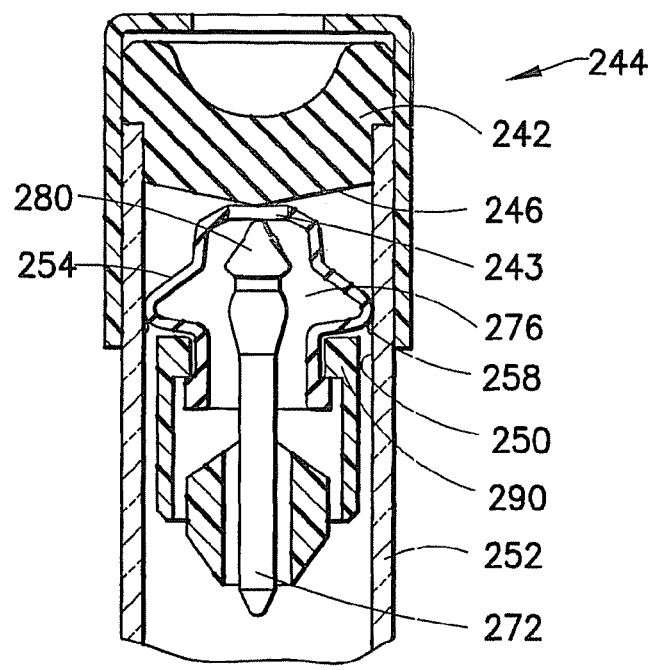
FIG. 23 is a cross-sectional view of an alternative mechanical separator engaged with a conventional stopper in the restraint position in accordance with an embodiment of the present invention.
Figure 24:
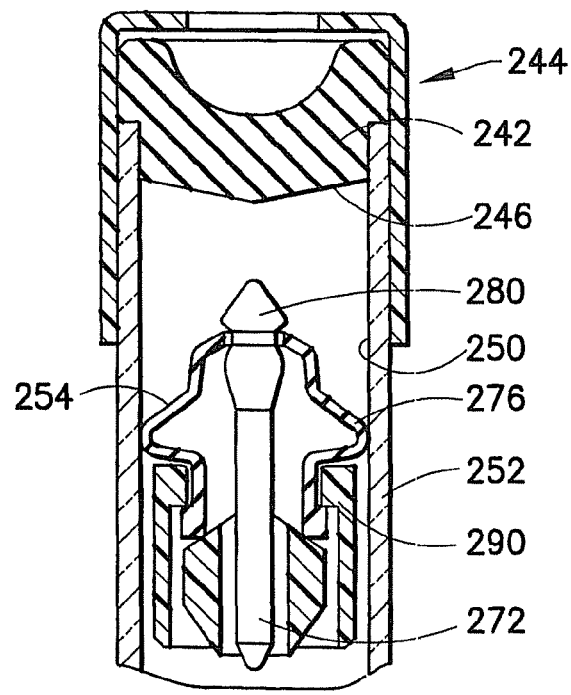
FIG. 24 is a cross-sectional view of the mechanical separator disengaged with the conventional stopper of FIG. 23 in the sealed position in accordance with an embodiment of the present invention.

Although the above invention has been described with specific reference to certain configurations, it is contemplated herein that various alternative structures may be employed without departing from the spirit of the claims herein. For example, as shown in FIGS. 23-24, although the previous description of the invention was made with reference to a closure having a bottom recess and/or a boss portion, the mechanical separator 244 can be configured to include a standard closure 242 having a conventionally sloped bottom surface 246. In this configuration, the deformable bellows 276, having an open passageway 243, is held in position adjacent the standard closure 242 by an interference fit between the interior wall 250 of the tube 252 and the outer surface 254 of the deformable bellows 276. Optionally, a small annular protrusion 258 in the interior wall 250 of the tube 252 may be employed to further increase the interference between the deformable bellows 276 and the tube 252. The ballast 290 is engaged with at least a portion of the deformable bellows 276. Also shown in FIGS. 23-24, it is contemplated herein that various configurations of the float 272 may also be employed, provided at least a portion of float 272, such as a head portion 280, is transitioned from a position within the interior of the deformable bellows 276 in restraint position, shown in FIG. 23, to a position exterior to the deformable bellows 276 in the sealed position, shown in FIG. 24.

Figure 25:
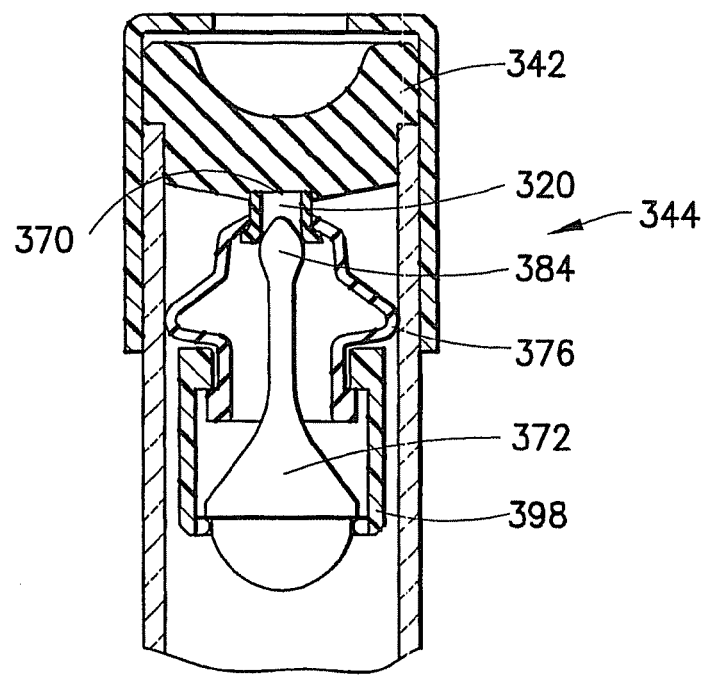
FIG. 25 is a cross-sectional view of a mechanical separator engaged with a conventional stopper and luer collar in the restraint position in accordance with an embodiment of the present invention.
Figure 26:
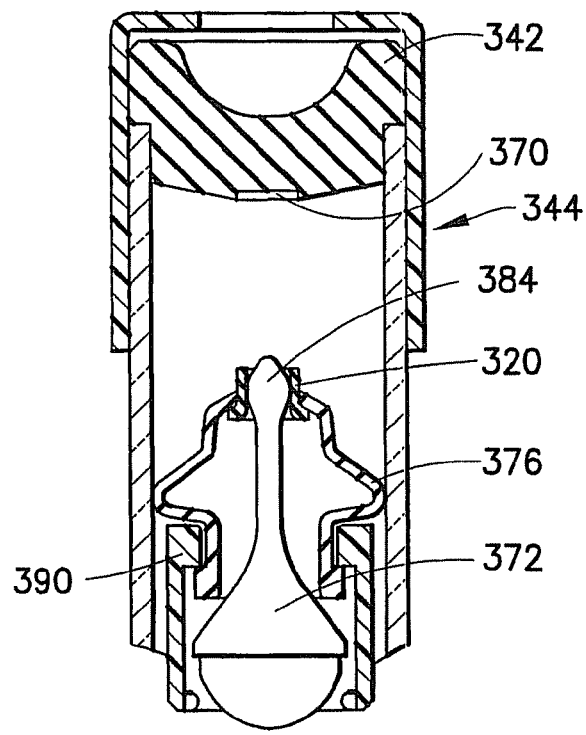
FIG. 26 is a cross-sectional view of the mechanical separator disengaged with the conventional stopper and luer collar of FIG. 25 in the sealed position in accordance with an embodiment of the present invention.

As shown in FIGS. 25-26, the mechanical separator 344 can be engaged with a closure 342 having a luer collar 320, which may be engaged into the underside of the closure 342. In one, embodiment, the luer collar 320 may be snap-engaged into the underside 370 of the closure 342. In use, when the mechanical separator 344 including a deformable bellows 376, a ballast 390 engaged with a portion of the deformable bellows 376, and a float 372 also engaged with a portion of the deformable bellows 376, is subject to centrifuge, the luer collar 320 may release from the underside 370 of the closure 342 along with the mechanical separator 344. Upon transition from the restraint position, shown in FIG. 25, to the sealed position, shown in FIG. 26, the head portion 384 of the float 372 of the mechanical separator 344 transitions from a position at least partially interior to the deformable bellows 376 to a position exterior to the deformable bellows 376 and into the luer collar 320.

Figure 27:
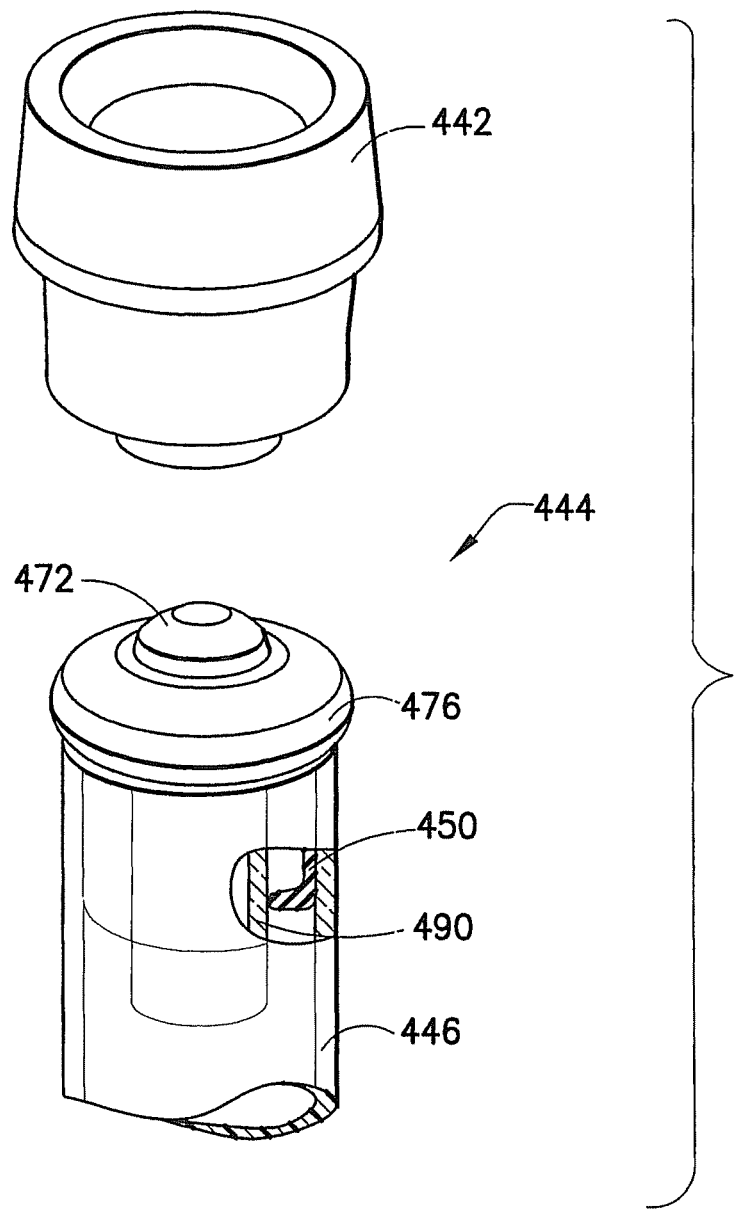
FIG. 27 is a partial cross-sectional partially exploded perspective view of a mechanical separation assembly including a closure, a mechanical separator in the sealed position, a tube insert, and a collection tube in accordance with an embodiment of the present invention.

As shown in FIG. 27, the mechanical separator 444, including a deformable bellows 476, a ballast 490 engaged with a portion of the deformable bellows 476, and a float 472 also engaged with a portion of the deformable bellows 476, may be inserted into a tube 446 having a tube insert 450. The tube insert 450 can be any appropriate device inserted into the tube 446, such as circumferentially disposed about a portion of the mechanical separator 444, to prevent premature release of the mechanical separator 444 from the tube insert 450 of the closure 442. In one embodiment, the tube insert 450 can be circumferentially disposed about a portion of the deformable bellows 476 to provide additional interference with the tube 476.

Figure 28:
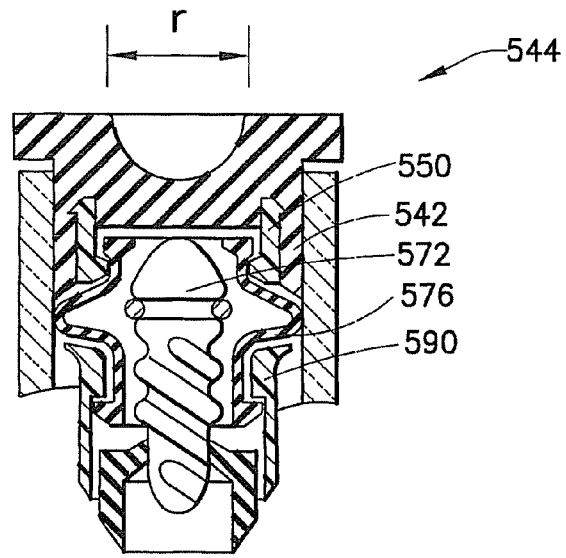
FIG. 28 is a partial cross-sectional front view of a mechanical separation assembly including a closure, a closure insert, a mechanical separator in the restraint position, and a collection tube in accordance with an embodiment of the present invention.

Alternatively, as shown in FIG. 28, the mechanical separator 544, including a deformable bellows 576, a ballast 590 engaged with a portion of the deformable bellows 576, and a float 572 also engaged with a portion of the deformable bellows 576 may be engaged with a retaining collar 550 that is permanently affixed to the underside of the closure 542. In one embodiment, the deformable bellows 576 is held fixed relative to the closure 542 during shipping and handling. The interior diameter "r" of the retaining collar 550 is sufficiently sized to allow access of a puncture tip for closure sampling after centrifugation (not shown), therethrough.

Figures 29, 30:
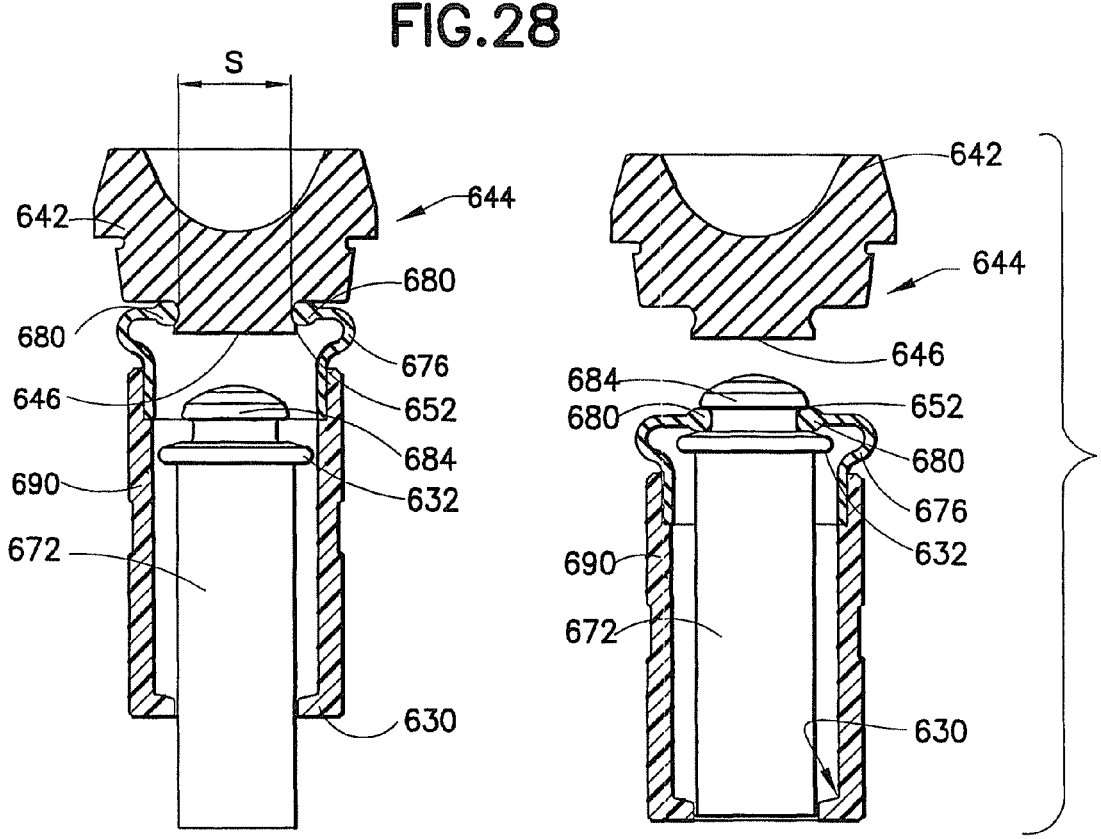
FIG. 29 is a cross-sectional view of a mechanical separator including a float, a deformable bellows having restraining shoulders, and a ballast in the restrained position with a closure in accordance with an embodiment of the present invention.
FIG. 30 is a cross-sectional view of the mechanical separator of FIG. 29 in the sealed position.

As shown in FIGS. 29-30, the mechanical separator 644 may also include a deformable bellows 676, a ballast 690 engaged with a portion of the deformable bellows 676, and a float 672 also engaged with a portion of the deformable bellows 676. In this embodiment, the deformable bellows 676 are biased over a boss portion 646 of the closure 642. In the restraint position, as shown in FIG. 29, the inner diameter "s" of the open passageway 652 of the deformable bellows 676 is enlarged to accommodate the boss portion 646. In the sealed position, shown in FIG. 30, the head portion 684 of the float 672 passes through the open passageway 652 to a location exterior to the deformable bellows 676 and is sealed therein by the unbiased diameter of the passageway 652. Optionally, the ballast 690 may include a shoulder 630 and the float 672 may include an engagement protrusion 632 for restraining the float 672 within the mechanical separator 644 during shipment in the restraint position.

Figure 31:
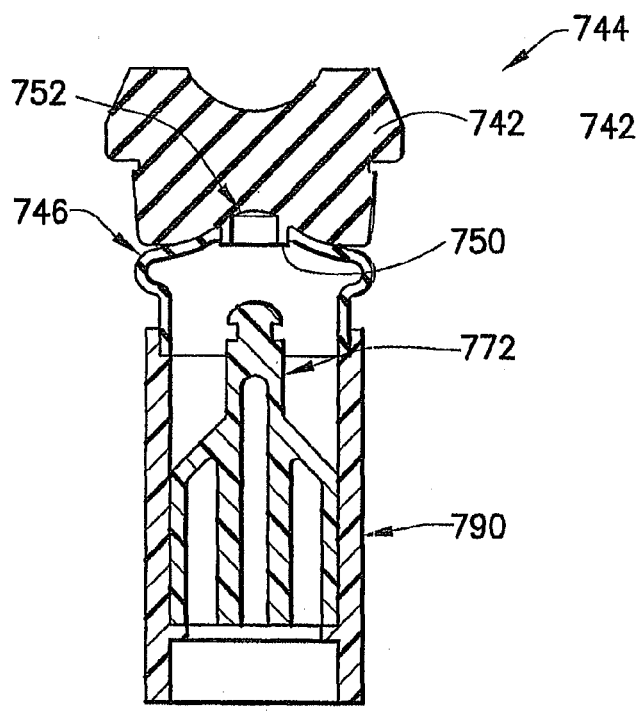
FIG. 31 is a cross-sectional view of a mechanical separator including an alternative float, a deformable bellows, and a ballast in the restrained position with a closure in accordance with an embodiment of the present invention.
Figure 32:
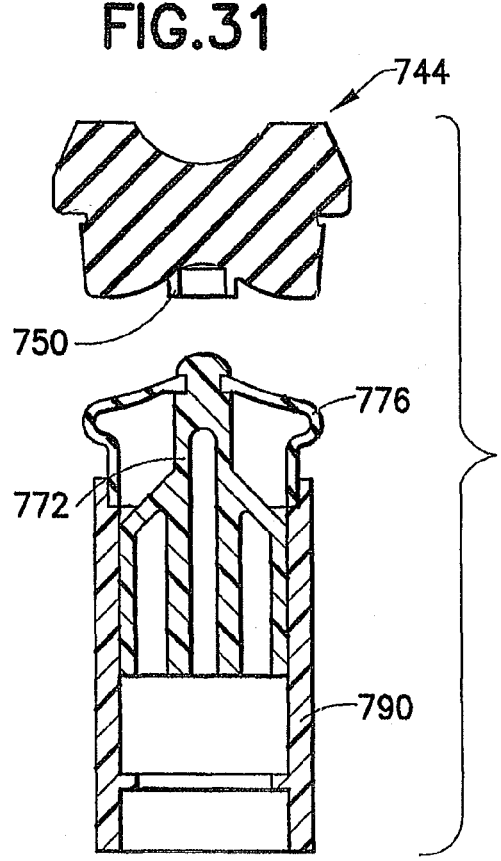
FIG. 32 is a cross-sectional view of the mechanical separator of FIG. 31 in the sealed position.

As shown in FIGS. 31-32, the mechanical separator 744 may include a deformable bellows 776, a ballast 790 engaged with a portion of the deformable bellows 776, and a float 772 also engaged with a portion of the deformable bellows 776. The closure 742 may include a ring 750 adjacent the contact surface 752 to further secure the deformable bellows 776 to the closure 742 in the restraint position, shown in FIG. 31. In this configuration, introduction of fluid, such as blood, causes the float 772 of the mechanical separator 744 to rise, and centrifugation causes the deformable bellows 776 to separate from the closure 742 and transitioning the mechanical separator 744 from the restraint position, shown in FIG. 31, to the closed position, shown in FIG. 32.

Figure 33:
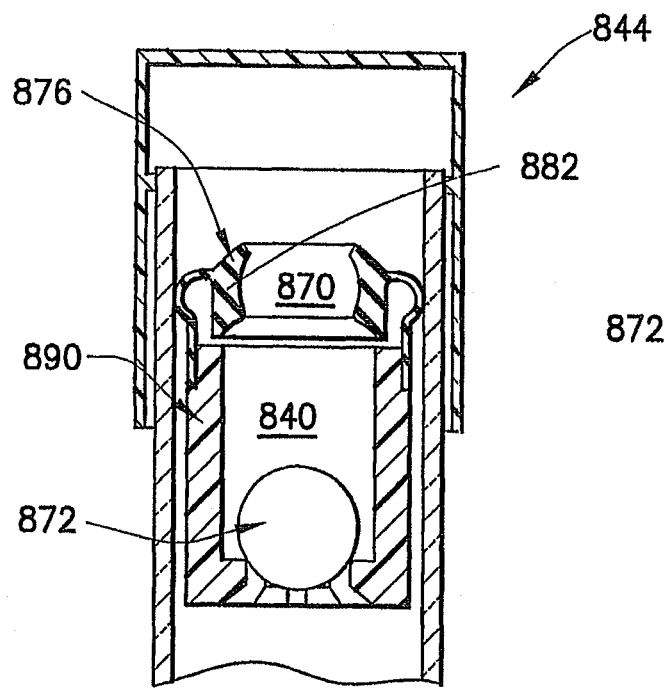
FIG. 33 is a cross-sectional view of a mechanical separator including a spherical float, a deformable bellows, and a ballast in the restrained position with a closure in accordance with an embodiment of the present invention.
Figure 34:
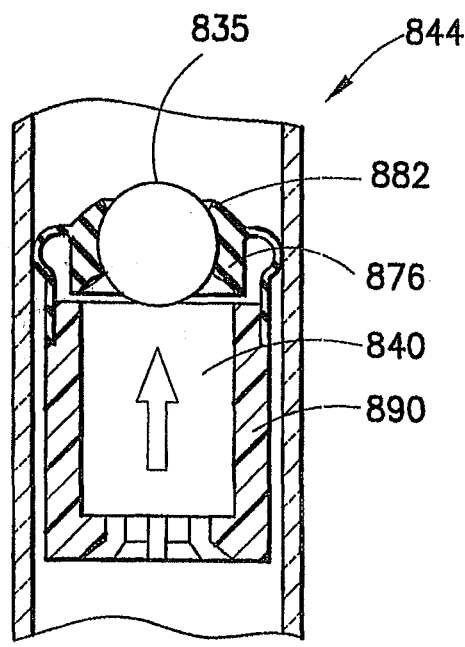
FIG. 34 is a cross-sectional view of the mechanical separator of FIG. 33 in the sealed position.

Alternatively, as shown in FIGS. 33-34, the mechanical separator 844 may include a deformable bellows 876, a ballast 890 engaged with a portion of the deformable bellows 876, and a substantially spherical float 872. In this embodiment, the open passageway 870 of the deformable bellows 876 includes protrusions 882 substantially corresponding to the outer diameter of the spherical float 872. In the restraint position, shown in FIG. 33, the spherical float 872 is positioned within the interior 840 of the mechanical separator 844. In the sealed position, shown in FIG. 34, the spherical float 872 includes a first portion 835 transitioned at least partially exterior to the interior 840 of the mechanical separator 844. In one embodiment, the spherical float 872 forms a seal with the protrusions 882 of the deformable bellows 876.

The mechanical separator of the present invention includes a float that is transitionable from a restraint position to a sealed position as the float and ballast exert opposing forces on the deformable bellows, thereby allowing the float to be received within the deformable bellows. Thus, in use, the mechanical separator of the present invention minimizes device pre-launch and reduces sample pooling under the closure by providing an open passageway within the bellows. Additionally, the reduced clearance between the exterior of the float and the interior of the ballast minimizes the loss of trapped fluid phases, such as serum and plasma.

Although the present invention has been described in terms of a mechanical separator disposed within the tube adjacent the open end, it is also contemplated herein that the mechanical separator may be located at the bottom of the tube, such as affixed to the bottom of the tube. This configuration can be particularly useful for plasma applications in which the blood sample does not clot, because the mechanical separator is able to travel up through the sample during centrifugation.

While the present invention is described with reference to several distinct embodiments of a mechanical separator assembly and method of use, those skilled in the art may make modifications and alterations without departing from the scope and spirit. Accordingly, the above detailed description is intended to be illustrative rather than restrictive. For example, while the assembly described above relates to a biological sample tube, other types of sample containers may be used. In addition, while various configurations of the components have been provided above, it should be noted that other shapes and dimensions may be implemented.

The invention claimed is:

1. A separation assembly for separating a fluid sample into a first phase and a second phase comprising:
   a collection container having an open end, a closed end, and a sidewall extending therebetween defining an interior;
   a closure adapted for sealing engagement with the open end of the collection container;
   a post engaged with the closure and adapted for positioning within the interior of the collection container; and
   a mechanical separator releasably engaged with the post, the mechanical separator having a passageway having a first open end and a second open end for allowing liquid to pass therethrough, and comprising:
   a float, having a first density; and a ballast, having a second density greater than the first density, wherein at least a portion of the mechanical separator is adapted to deform upon application of rotational force and a portion of the post is received within the first open end of the mechanical separator and the mechanical separator is adapted to transition from a first initial position in which the passageway allows fluid to pass therethrough, to a second sealed position in which fluid is prevented from passing through the passageway, upon applied rotational force.

2. The separation assembly of claim 1, wherein the ballast is circumferentially disposed about a section of the float and longitudinally moveable with respect to the float.

3. The separation assembly of claim 1, wherein the ballast comprises an exterior surface and defines an annular shoulder circumferentially disposed within the exterior surface.

4. The separation assembly of claim 1, wherein at least a portion of a first end of the mechanical separator is structured for receipt within the closure.

5. The separation assembly of claim 1, wherein the float comprises polypropylene, and the ballast comprises polyethylene terephthalate.

6. The separation assembly of claim 1, further comprising a deformable bellows defining the passageway.

7. The separation assembly of claim 6, wherein the ballast is engaged with the deformable bellows.

8. The separation assembly of claim 6, wherein the float is positioned within an interior of the deformable bellows and is transitionable from a restraint position where the passageway is open to a sealed position where the float engages the deformable bellows to seal the passageway.

9. The separation assembly of claim 8, wherein the mechanical separator is oriented such that a first portion of the float is positioned below a first end of the deformable bellows in the restraint position, and the first portion of the float is positioned above the first end of the deformable bellows in the sealed position.

10. The separation assembly of claim 8, wherein the transition from the restraint position to the sealed position occurs as the float and ballast exert opposing forces on the deformable bellows.

11. The separation assembly of claim 8, wherein the transition from the restraint position to the sealed position further includes advancing the float within the passageway of the deformable bellows.

12. The separation assembly of claim 8, wherein the float and deformable bellows form a liquid impermeable seal in the sealed position.

13. The separation assembly of claim 6, wherein the float comprises an engagement protrusion and the deformable bellows comprises a restraint shoulder, the engagement protrusion of the float restrained within the deformable bellows by the restraint shoulder.

14. The separation assembly of claim 6, wherein the ballast comprises an interlock recess for accommodating a portion of the deformable bellows for attachment thereto.

15. The separation assembly of claim 6, wherein the deformable bellows comprises a thermoplastic elastomer.

16. The separation assembly of claim 1, wherein the mechanical separator is adapted to transition from a first initial position in which a portion of the post is disposed within the passageway and a second position in which the mechanical separator is disengaged from the post, upon applied rotational force.

* * * * *